United States Patent
Wang et al.

(10) Patent No.: US 7,125,850 B2
(45) Date of Patent: Oct. 24, 2006

(54) METHODS OF IDENTIFYING INHIBITORS OF GADD45 POLYPEPTIDE ACTIVITY, AND INHIBITORS OF SUCH ACTIVITY

(75) Inventors: Xin Wei Wang, Rockville, MD (US); Curtis C. Harris, Garrett Park, MD (US); Albert J. Fornace, Jr., Bethesda, MD (US); Jill D. Coursen, Boston, MA (US); Qimin Zhan, Pittsburgh, PA (US)

(73) Assignee: The United States of America as represented by the Department of Health and Human Sevices, Washington, DC (US)

( * ) Notice: Subject to any disclaimer, the term of this patent is extended or adjusted under 35 U.S.C. 154(b) by 0 days.

(21) Appl. No.: 11/297,160

(22) Filed: Dec. 7, 2005

(65) Prior Publication Data
US 2006/0088888 A1    Apr. 27, 2006

Related U.S. Application Data

(62) Division of application No. 10/600,158, filed on Jun. 20, 2003, now Pat. No. 7,005,419, which is a division of application No. 09/534,811, filed on Mar. 24, 2000, now Pat. No. 6,613,318.

(60) Provisional application No. 60/126,069, filed on Mar. 25, 1999.

(51) Int. Cl.
*A61K 38/00* (2006.01)
*A61K 38/04* (2006.01)
*C07K 7/00* (2006.01)

(52) U.S. Cl. ............ 514/17; 514/12; 514/13; 514/15; 514/16; 530/329; 530/324; 530/326; 530/327; 530/328

(58) Field of Classification Search ............ None
See application file for complete search history.

(56) References Cited

OTHER PUBLICATIONS

Ren, M. et al., "Effects of mutant ran/TC proteins on cell cycle progression," *Molecular and Cellular Biology*, Jun. 1994, pp. 4216-4224, vol. 14(6).

Richards, S.A. et al., "The C terminus of the nuclear RAN/TC4 GTPase stabilizes the GDP-bound state and mediates interactions with RCC, RAN-GAP and HTF9A/RANBP1," *Journal of Biological Chemistry*, 1995, pp. 14405-14411, vol. 270(24).

Smith, M.L. et al., "Antisense GADD45 expression results in decreased DNA repair and sensitizes cells to u.v.-irradiation of cisplatin," *Oncogene*, 1996, pp. 2255-2263, vol. 13.

Takekawa, M. and Saito, H., "A family of stress-inducible GADD45-like proteins mediate activation of the stress-responsive MTK1/MEKK4 MAPKKK," *Cell*, Nov. 13, 1998, pp. 521-530, vol. 95.

Yang, Q. et al., "Mechanisms of a GADD45-mediated G2/M checkpoint," AACR special conference, Genetic and Functional Consequences of Cell Cycle Alteration in Cancer, Oct. 20-24, 1999, San Diego, California, USA.

Zhan, Q. et al., "Association with Cdc2 and inhibition of Cdc2/Cyclin B1 kinase activity by the p53-regulated protein Gadd45," *Oncogene*, 1999, pp. 2892-2900, vol. 18.

Zhan, Q. et al., "Tumor suppressor p53 can participate in transcriptional induction of the GADD45 promoter in the absence of direct DNA binding," *Molecular and Cellular Biology*, May 1998, pp. 2768-2778, vol. 18(5).

*Primary Examiner*—B. Dell Chism
(74) *Attorney, Agent, or Firm*—Townsend and Townsend and Crew LLP

(57) ABSTRACT

The present invention is directed to novel methods for assaying for modulators of GADD45 polypeptide activity. The invention also provides means to sensitize a proliferating cell to a DNA base-damaging agent by administration of novel inhibitors of GADD45 polypeptide activity. The invention further provides polypeptides which interfere with the ability of Cdc2/cyclin B1 complexes to cause a pause at the G2/M stage of the cell cycle in response to GADD45, and nucleic acids which encode such polypeptides.

8 Claims, 5 Drawing Sheets

A

| | Box I | | | | |
|---|---|---|---|---|---|
| hGADD45 | MTLEEFSAGE---QKTERMDKVGDALEEVLSKALSQRTITVGVYEAAKLLNVDPDNVVLC | 57 |
| hGADD45β | MTLEELVACD---NAAAQKMQTVTAAVEELLVAAQRQDRLTVGVYESAKLMNVDPDSVVLC | 57 |
| hGADD45γ | MTLEEVRGQDTVPESTARMQGAGKALHELLLSAQRQGCLTAGVYEAKVLNVDPDNVTFC | 60 |
| mGADD45 | MTLEEFSAAE---QKTERMDTVGDALEEVLSKARSQRTITVGVYEAAKLLNVDPDNVVLC | 57 |
| rGADD45 | MTLEEFSAAE---QKTERMDTVGDALEEVLSKARSQRTITVGVYEAAKLLNVDPDNVVLC | 57 |

Box II

| | Box II | |
|---|---|---|
| hGADD45 | LLAADEDDDRDVALQIHFTLIQAFCCENDINILRVSNPGRLAELLLLETDAGPAASEGAE | 117 |
| hGADD45β | LLAIDEEEDDIALQIHFTLIQSFCCDNDINIVRVSGMQRLAQLLGEPAETQGTTEAR---- | 115 |
| hGADD45γ | VLAAGEDEGDIALQIHFTLIQAFCCENDIDIVRVGDVQRLAAIVGAGEAGAPG------ | 115 |
| mGADD45 | LLAADEDDDRDVALQIHFTLIRAFCCENDINILRVSNPGRLAELLLENDAGPAESGGAA | 117 |
| rGADD45 | LLAADEDDDRDVALQIHFTLIRAFCCENDINILRVSNPGRLAELLLLENDKSPAESGGLA | 117 |

Box III

| | Box III | |
|---|---|---|
| hGADD45 | QPPDLHCVLVTNPHSSQWKDPALSQLICFCRESRYMDQWVPVINLPER | 165 |
| hGADD45β | ---DLHCLLVTNPHTDAWKSHGLVEVASYCEESRGNNQWVPYISLQER | 160 |
| hGADD45γ | ---DLHCILISNPNEDAWKDPALEKLSLFCEESRSVNDWVPSITLPE- | 159 |
| mGADD45 | QTPDLHCVLVTNPHSSQWKDPALSQLICFCRESRYMDQWVPVINLPER | 165 |
| rGADD45 | QTPDLHCVLVTNPHSSQWKDPALSQLICFCRESRYMDQWVPVINLPER | 165 |

```
                    61                      81
                    |                       |
WT      .LLAA DEDDDR DVALQI HFTLIQAF CCENDI NILR.
M62-67  .LLAA AAAAAA DVALQI HFTLIQAF CCENDI NILR.
M74-79  .LLAA DEDDDR DVALQI AAAAAAF CCENDI NILR.
M82-87  .LLAA DEDDDR DVALQI HFTLIQAF AAAAAA NILR.
```

B ant DNA before entry into mitosis it can avoid suicidal apoptosis. To gain sufficient repair time after detecting that its chromosomes have been damaged, the cell "stalls" its cell cycle at a stage just before entry into mitosis. If the damage is too great, not enough repair can be done and
METHODS OF IDENTIFYING INHIBITORS OF GADD45 POLYPEPTIDE ACTIVITY, AND INHIBITORS OF SUCH ACTIVITY

CROSS REFERENCE TO RELATED APPLICATIONS

This application is a division of U.S. Ser. No. 10/600,158, filed Jun. 20, 2003 now U.S. Pat No. 7,005,419, which is a division of U.S. Ser. No. 09/534,811, filed Mar. 24, 2000, now U.S. Pat. No. 6,613,318, which claims priority from provisional application no. 60/126,069, filed Mar. 25, 1999, the contents of all above-named applications are incorporated herein by reference.

STATEMENT REGARDING FEDERALLY SPONSORED RESEARCH OR DEVELOPMENT

Not applicable.

FIELD OF THE INVENTION

The present invention is generally related to inhibiting the growth or proliferation of cancerous cells. In particular, the invention is directed to novel methods for assaying for modulators of GADD45 polypeptide activity. The invention also provides means to sensitize a proliferating cell to a DNA base-damaging agent by administration of novel inhibitors of GADD45 polypeptide activity, and compositions which modulate GADD45 polypeptide activity.

BACKGROUND TO THE INVENTION

A common method to treat cancer is to give radiation or chemicals to damage the cancer cell's chromosomes (DNA) so badly that the cell dies. These treatments are, however, equally toxic to cells growing normally. It is difficult or impossible under most circumstances to limit a patient's exposure to the DNA damaging agent to only the cancer cells. One way to protect normally growing cells from the toxic anti-cancer treatment would be to simultaneously treat the cancer cells with a second agent whose activity reduces the amount of toxic radiation or chemical needed to be effective. This could be done by "sensitizing" the cancer to the toxic treatments so the growing tumor cells die when a smaller amount of toxic radiation or chemical is administered.

One way to "sensitize" an undesirable growing cell (such as a cancer cell) to a DNA-damaging agent is to manipulate the cell so it will die when it incurs less DNA damage. A proliferating cell can detect if and how much chromosome damage it has. If there is enough DNA damage, a normal cell commits suicide, killing itself by a preprogrammed cell death mechanism called "apoptosis." This suicidal reaction is a protective mechanism because damaged DNA can result in mutation of genes and disease, such as cancer (Hartwell (1994) Science 266:1821–1828).

A damaged cell, however, actively tries to avoid suicide by repairing the chromosomal damage inflicted by the toxic treatments. By using its DNA repair machinery, the cell can save itself from what otherwise would be a suicide-initiating dose of radiation or base-damaging agent (Smith (1996) Mutation Research 340:109–124).

One avenue by which a cell can repair enough DNA damage to "save itself" from a suicidal fate takes advantage of the fact that the programmed cell death signal is triggered only at the stage of the cell's growth where its chromosomes begin to divide (called "mitosis"). If the cell has the time to repair enough damaged DNA before entry into mitosis it can avoid suicidal apoptosis. To gain sufficient repair time after detecting that its chromosomes have been damaged, the cell "stalls" its cell cycle at a stage just before entry into mitosis. If the damage is too great, not enough repair can be done and the cell dies (Paulovich (1997) Cell 88:315–321; O'Connor (1997) Cancer Surveys 29:151–182). Under "normal" circumstances, with an intact DNA repair and cell cycle "stalling" mechanisms, relatively larger of amounts of toxic agent must be administered -to kill the growing cell. However, if this stalling mechanism can be disturbed, less DNA repair time is available, less DNA damage is fixed before entry into mitosis, and thus relatively lesser amounts of anti-cancer agent are needed to kill the cell. Thus, discovery of inhibitors of this stalling mechanism, and their co-administration with DNA base-damaging agents, would provide novel means of effectively treating cancer with lower doses of toxic agents.

G2/M checkpoints prevent the segregation of damaged chromosomes, which is likely to be important in human tumorigenesis. (Hartwell, L. H. and M. B. Kastan, *Science* 266:1821–1828 (1994); Paulovich, A. G., et al. *Cell* 88:315–321 (1997).) The transition from G2 to M is regulated, in part, by the G2-specific kinase consisting of Cdc2 and cyclin B1. (Nurse, P., *Cell* 79:547–550 (1994).) Many G2/M regulatory genes have been identified recently, such as Chk1, Chk2, ATM (MEC1 and TEL1 in *S. cerevisiae* and RAD3 in *S. pombe*) and the 14-3-3 family. (Agarwal, M. L., et al., *Proc. Natl. Acad. Sci.* USA 92:8493–8497 (1995); Elledge, S. J., *Science* 274:1664–1672 (1996); Morrow, D. M., et al., *Cell* 82:831–840 (1995); Paulovich, A. G., et al. supra; Savitsky, K., et al., *Science* 268:1749–1753 (1995); Weinert, T. A., et al., *Genes Dev.* 8:652–665 (1994).) Their products alter Cdc2 activity by inhibiting dephosphorylation of inhibitory sites on Cdc25C. p53 also has been implicated in an IR-induced G2/M checkpoint. (Agarwal, M. L., et al., supra; Bunz, F., A., et al., *Science* 282:1497–1501 (1998); Guillouf, C., et al., *Oncogene* 10:2263–2270 (1995); Powell, S. N., et al., *Cancer Res* 55:1643–1648 (1995); Stewart, N., et al., *Oncogene* 10:109–115 (1995).) It may modulate the G2/M transition by upregulating 14-3-3σ (12) and/or p21$^{waf1}$. (Bunz, F., A., et al., *Science* 282:1497–1501 (1998); Dulic, V., et al., *Mol. Cell Biol* 18:546–557 (1998); Medema, R. H., et al., 16:431–441 (1998).) Consequently, cells lacking p53 show chromosome instability (Fukasawa, K., et al., *Science* 271:1744–1747 (1996)), a phenotype likely resulting from defects in the G2/M checkpoint. Therefore, a multiplicity of G2/M checkpoints in response to DNA damage may well involve redundant controls involving both p53-independent and p53-dependent pathways.

GADD45 is a 165-amino acid nuclear protein whose expression also is p53-dependent (Zhan, Q., et al., *Mol. Cell Biol* 13:4242–4250 (1993)). GADD45 was originally identified on the basis of a rapid induction in Chinese hamster ovarian cells after UV irradiation (Fomace, A. J., Jr., et al. *Mol. Cell Biol* 9:4196–4203 (1989).). Induction of GADD45 also was observed following treatment with many other types of DNA-damaging agents, including various environmental stresses, hypoxia, IR, genotoxic drugs and growth factor withdrawal. (Papathanasiou, M. A., et al., *Mol. Cell Biol* 11:1009–1016 (1991)). In mammalian cells, two additional family members with extensive sequence homology, GADD45β and GADD45γ, were identified recently. (Takekawa, M. and H. Saito, *Cell* 95:521–530 (1998).) Similar to p53-deficient cells, cells from Gadd45-deficient mice also show genomic instability, including chromosome abnormalities and centrosome amplification. (Hollander, M. C., et al., *Nat. Genet* 23:176–184 (1999).) It is known that GADD45 binds to PCNA, p21$^{waf1}$ and Cdc2. (Kearsey, J. M., et al., *Oncogene* 11:1675–1683 (1995); Smith, M. L., et al., *Science* 266:1376–1380 (1994); Zhan, Q., et al., *Oncogene* 18:2892–2900 (1999).) GADD45 has no inhibitory effect on the kinase activity of the G1-specific Cdk2/cyclin E complex. (Smith, M. L., et al., *Science* 266:1376–1380 (1994); Zhan, Q., et al., *Oncogene* 18:2892–2900 (1999).) Increased expression of GADD45 in primary human fibroblasts arrests cells at the G2-M boundary. This arrest was attenuated by the overexpression of cyclin B1 and Cdc25C.

Thus, GADD45 is a mediator of the G2-M stalling mechanism. It has been reported that blocking GADD45 expression by constitutive antisense oligonucleotide expression "sensitized" a human colon carcinoma cell line to killing by UV irradiation and by cisplatin, a DNA-damaging cancer chemotherapy drug (Smith (1996) Oncogene 13:2255–2263). Identification of novel modulators, particularly inhibitors, of GADD45 polypeptide activity would provide new means to inhibit proliferation of cancer cells. The invention fills these, and other, needs.

SUMMARY OF THE INVENTION

The invention provides various in vitro methods of assaying for modulators of GADD45 polypeptide activity. In one embodiment, the method comprises combining a GADD45 polypeptide with a test compound in an aqueous solution and assaying whether the test compound can inhibit or decrease GADD45 polypeptide binding specifically to a Cdc2 polypeptide. In another in vitro embodiment, the method comprises combining a GADD45 polypeptide with a test compound in an aqueous solution and assaying whether the test compound can inhibit or decrease GADD45 polypeptide-mediated dissociation of a Cdc2/Cyclin B1 protein complex. In one embodiment, the method comprises combining a GADD45 polypeptide with a test compound in an aqueous solution and assaying whether the test compound can inhibit or decrease the ability of GADD45 polypeptide to bind specifically to chromatin. In another embodiment, the method comprises combining a GADD45 polypeptide with a test compound in an aqueous solution and assaying whether the test compound can inhibit or decrease GADD45 polypeptide inhibition of histone phosphorylation by a Cdc2/Cyclin B1 complex. In alternative embodiments, the GADD45 polypeptide is a subsequence of the full length protein (SEQ ID NO:2) that includes all or part of an required for GADD45 activity, for an active site or for a protein:protein binding domain, such as, e.g., a peptide having a sequence as set forth by amino acid residues 71 to 124, or 61 to 87, or 71 to 87, or 61 to 124, of SEQ ID NO:2.

The invention also provides an in vitro method of assaying for a compound capable of specifically binding to a GADD45 polypeptide, wherein the method comprises combining a GADD45 polypeptide with a test compound in an aqueous solution and assaying whether the test compound specifically binds to the GADD45 polypeptide. In alternative embodiments, the GADD45 polypeptide is a subsequence of the full length protein that includes all or part of an active site or protein:protein binding domain, such as, e.g., a peptide having a sequence as set forth by amino acid residues 71 to 124, or 61 to 87, or 71 to 87, or 61 to 124, of SEQ ID NO:2.

The invention also provides in vivo methods of assaying for a modulator of GADD45 polypeptide activity. In one embodiment, the method comprises combining a cell expressing a GADD45 polypeptide with a test compound in an aqueous solution and assaying whether the test compound can inhibit or decrease GADD45 polypeptide binding specifically to a Cdc2 polypeptide. In another embodiment, the method comprises combining a cell expressing a GADD45 polypeptide with a test compound in an aqueous solution and assaying whether the test compound can inhibit or decrease GADD45 polypeptide-mediated dissociation of a Cdc2/Cyclin B1 protein complex. The cells can be proliferating cells, such as cancer cells.

The invention provides methods for sensitizing a proliferating cell to a DNA base-damaging agent by inhibiting GADD45 polypeptide activity. In one embodiment, the method comprises administering a composition capable of specifically binding to a GADD45 polypeptide in an amount sufficient to inhibit or decrease GADD45 polypeptide specific binding to the Cdc2 polypeptide. Another embodiment comprises administering a composition capable of specifically binding to the GADD45 polypeptide in an amount sufficient to inhibit or decrease GADD45-mediated dissociation of a Cdc2/Cyclin B1 protein complex. In these methods, the composition can be an antibody specifically reactive with the GADD45 polypeptide. In one embodiment, the antibody is specifically reactive with a GADD45 active site or protein:protein binding domain. In alternative embodiments, the GADD45 is a subsequence of the full length protein that includes all or part of an active site or protein:protein binding domain or a site required for GADD45 polypeptide activity, such as, e.g., a peptide having a sequence as set forth by amino acid residues 71 to 124, or 61 to 87, or 71 to 87, or 61 to 124, of SEQ ID NO:2. In various embodiments, the proliferating cell can be a cancer cell; the DNA base-damaging agent can be UV radiation or a DNA base-damaging agent such as a chemotherapeutic agent, and the chemotherapeutic agent can be a base-damaging alkylating agent.

The invention also provides inhibitors of GADD45 polypeptide activity in the form of GADD45 peptides comprising sequences which are required for GADD45 activity. These GADD45 peptides, when administered to a cell, interfere with the ability of GADD45 to inhibit a Cdc2/ cyclin B1 protein complex from phosphorylating histone H1. In alternative embodiments, the blocking GADD45 peptides comprise amino acids 62–67 of SEQ ID NO:2, and can, for example, have a sequence as set forth by amino acid residues 61 to 87 of SEQ ID NO:2. Alternatively, they can be other subsequences of the GADD45 protein which comprise the DEDDDR (SEQ ID NO:5) acidic motif (amino acid residues 62–67 of GADD45) and a portion of the native sequence of SEQ ID NO:2 flanking that motif on the amino or the carboxyl sides, or both. In various embodiments, the GADD45 peptides can be 10, 20, 30, 40, 50 or 60 amino acid residues in length. These peptides, like the GADD45 binding inhibitors of the invention, can be co-administered with cancer therapeutic agents, particularly those which damage DNA (as, e.g., UV irradiation or chemotherapeutic agents such as cisplatin) to sensitize proliferating cells to the DNA damaging anti-cancer agent. The invention further provides polypeptides which interfere with or inhibit the ability of GADD45 to reduce or eliminate phosphorylation of histone H1. Typically, such polypeptides also comprise the acidic motif DEDDDR (SEQ ID NO:5).

The polypeptides of the invention can be in a pharmaceutically acceptable carrier, and can be loaded into liposomes or otherwise protected from exposure to proteases before they reach an intended site of action. The invention also provides nucleic acids encoding the polypeptides and for the administration of the polypeptides or the nucleic acids encoding them to inhibit the growth or proliferation of cancer cells by rendering them more sensitive to chemotherapeutic agents or to radiation therapy.

DETAILED DESCRIPTION OF THE INVENTION

Introduction

Figure 1B:
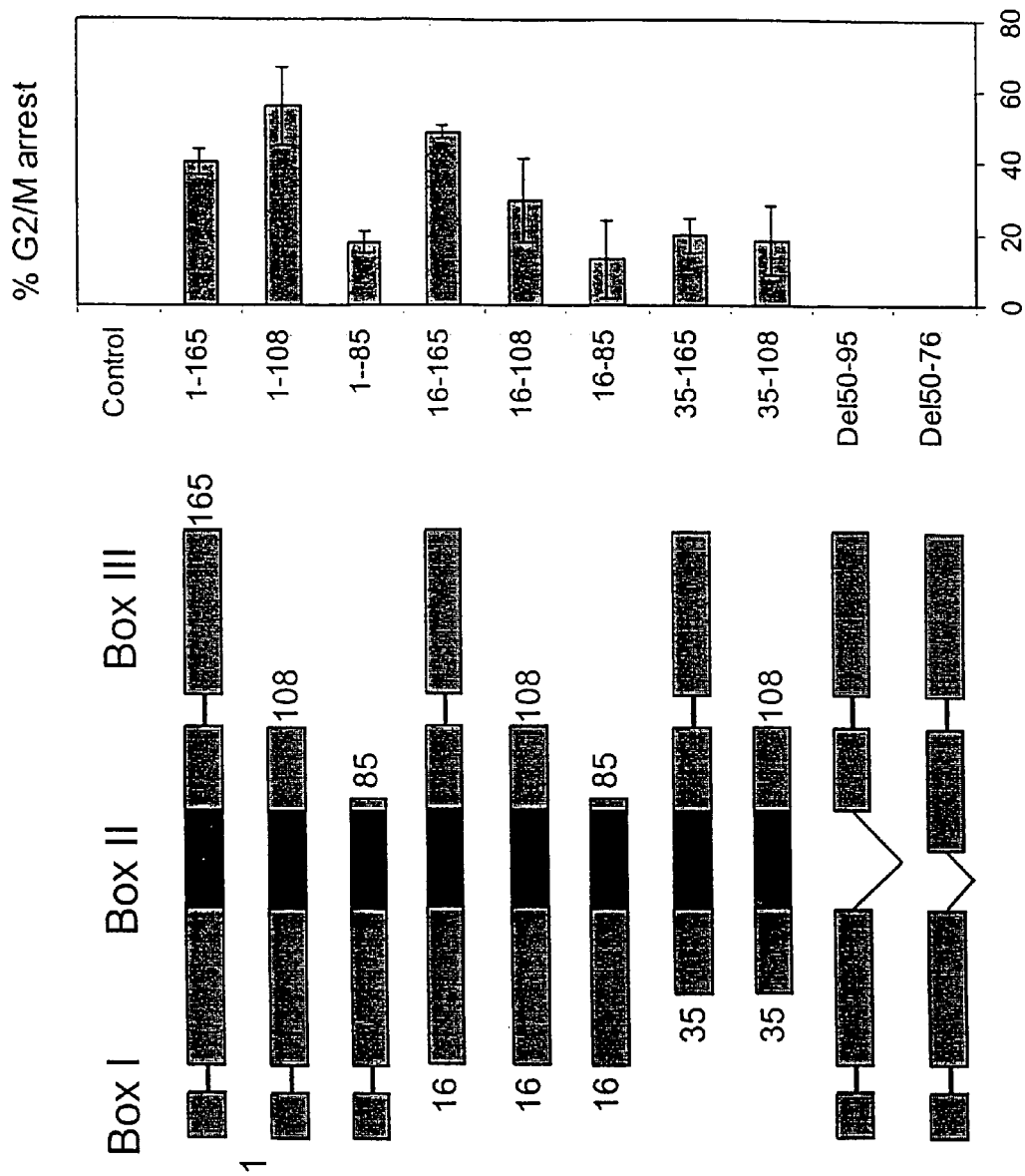
FIG. 1. Mapping of the functional domain of GADD45 required for G2/M arrest. (A) Sequence comparison of the human mouse and rat GADD45 family members was made with the multiple alignment module of the DNASTAR software. The GenBank accession numbers of these sequences are as follows: hGADD45 (SEQ ID NO:2), NM_001924; hGADD45β (SEQ ID NO:6), AF078077; hGADD45γ (SEQ ID NO:7), AF078078; mGADD45 (SEQ ID NO:8), B56535; rGADD45 (SEQ ID NO:9), L32591 (h, human; m, mouse; r, rat). (B) The activities of the GADD45 deletion mutants. Different parts of the N-terminus, C-terminus or the central region of GADD45 were deleted. The mutants were introduced into normal human fibroblast cells via microinjection to determine their ability to induce a G2/M arrest. The data are averages from at least three independent experiments. Error bars represent one standard deviation.
Figures 2A, 2B:
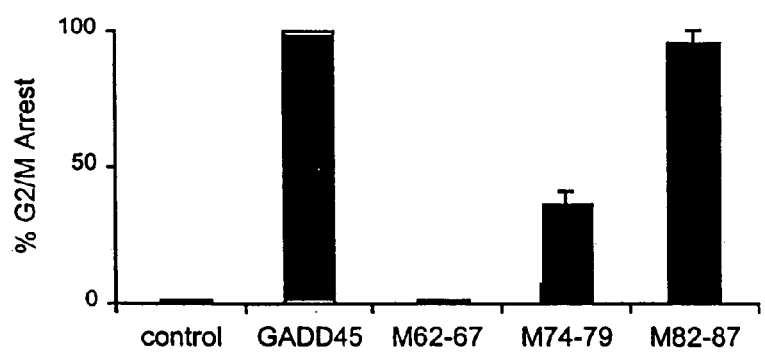
FIG. 2. Ability of site mutagenesis mutants to induce a G2/M arrest. (A) Sequence composition of GADD45 between residues 58 and 91. The three regions targeted for mutagenesis are underlined (WT=SEQ ID NO:10). These regions were chosen based on their extensive conservation among the members of the GADD45 family. Site-directed mutagenesis was used to change residues 62–67 (M62–67; SEQ ID NO: 11), 74–79 (M74–79; SEQ ID NO: 12), or 82–87 (M82–87; SEQ ID NO: 13) t0 alanines. (B) The mutants were expressed in normal primary human fibroblasts via microinjection and the percentage of mutant-expressing cells that arrested at G2/M were determined after 24 h. Results are an average of three separate experiments Error bars represent one standard deviation.
Figures 3A, 3B:
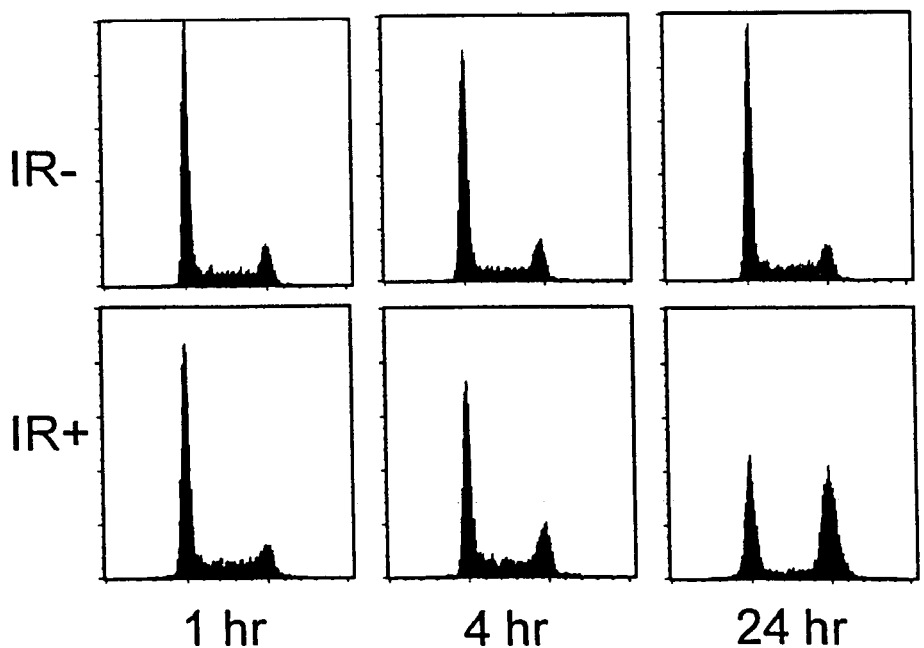
FIG. 3. Cdc2/cyclin B1 kinase assay in RKO cells treated with ionizing radiation or transfected with GADD45 mutants. (A) RKO cells were irradiated with 6.3 Gy of IR or left untreated and were harvested at 1, 4 and 24 h. One mg of protein was immunoprecipitated with the anti-cyclin B1 antibody, and histone H1 kinase assays were performed. Anti-mouse IgG was used as a negative control. (B) Cells in parallel with (A) were collected and subjected to cell cycle analysis by FACS. The percent of cells at G1, S or G2/M of the cell cycle are indicated in panel A. (C) The ability of the GADD45 mutants to inhibit Cdc2/cyclin B1 kinase activity in vivo. RKO cells were transfected with wild-type or mutant GADD45. Cells were collected 6 and 24 h later and the Cdc2/cyclin B1 kinase activity was measured. An empty plasmid vector was used as a control. The amount of phosphorylated histone H1 was quantified with a Fuji Bas2500 phosphorimaging system. The data were normalized to the control lane and are expressed as percent of inhibition.
Figure 3C:
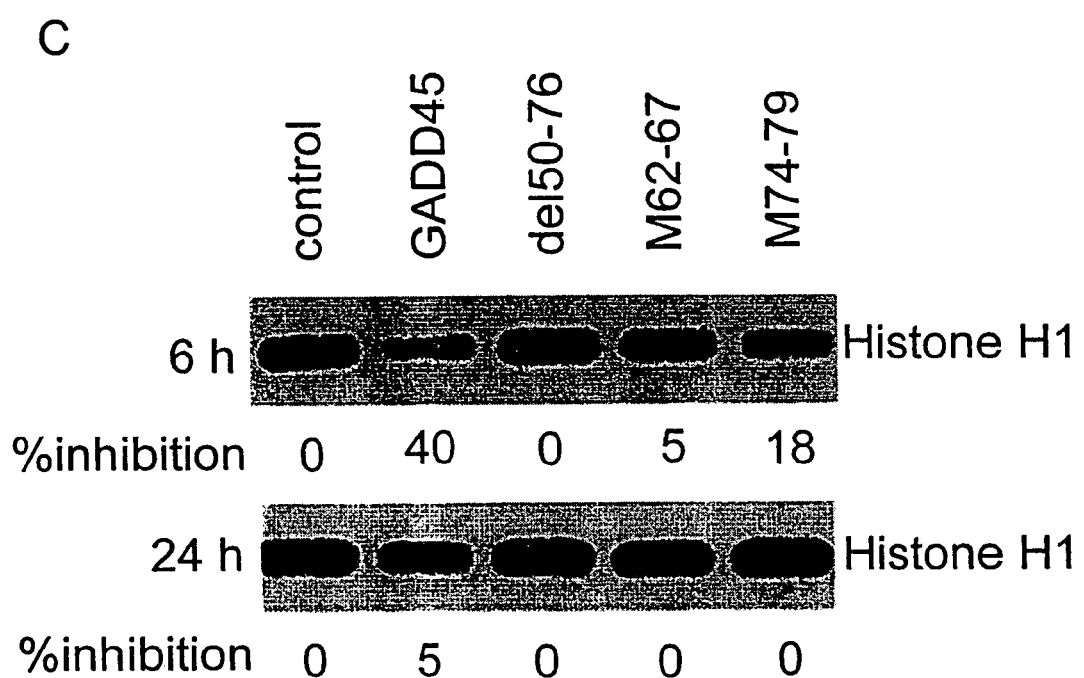

The present invention demonstrates that GADD45 activates a G2/M checkpoint after damage induced by either UV radiation or alkylating agents, but is not involved in a G2/M checkpoint induced by ionizing radiation. Increased expression of GADD45 in normal human fibroblasts arrests the cells in G2/M. The data presented herein demonstrate that the amino and carboxyl termini of GADD45 are dispensable for the G2/M arrest, but that the central region (residues 50–76) is required. Further, the invention demonstrates that a unique acidic motif, DEDDDR (SEQ ID NO:5), in this region plays a key role in the inhibition of Cdc2/cyclin B1 kinase activity and in the induction of a G2/M arrest. Polypeptides of this acidic motif or comprising this motif can serve as small molecule, dominant negative inhibitors of GADD45 activity.

The present invention provides novel means for identifying compositions that bind GADD45 polypeptides and act as modulators of GADD45 polypeptide activity. These new means are based on the invention's discovery of the mechanisms by which GADD45 acts to enhances a cell's ability to repair DNA damage. Inhibiting GADD45 polypeptide activity diminishes the time for, and thus amount of, DNA repair completed before entering mitosis. As a result, with co-administration of a GADD45 polypeptide inhibitor, less of a toxic DNA damaging anti-cancer agent is needed to trigger the suicidal apoptosis mechanism to kill the growing cancer.

While inhibitory phosphorylation of Cdc2 and suppression of cyclin B1 levels were known to be involved in G2/M cell cycle delays after genotoxic stress, the invention for the first time demonstrates that GADD45 directly inhibits the histone kinase activity of the Cdc2/Cyclin B1 complex. Thus, the invention provides a means to identify a modulator of GADD45 activity by determining its ability to modify GADD45 polypeptide-mediated inhibition of Cdc2/Cyclin B1 complex kinase activity, particularly the phosphorylation of histones, such as histone H1.

The invention also for the first time demonstrates that GADD45 physically interacts with Cdc2, but not Cyclin B1. The invention also identifies for the first time the Cdc2 binding domain of the GADD45 polypeptide. Thus, the invention provides a novel means to identify compositions that bind to GADD45, or to the GADD45 binding site on Cdc2, and modulate GADD45 activity by determining their ability to attenuate or enhance the binding of GADD45 polypeptide to the Cdc2 polypeptide.

The invention also demonstrates that addition of GADD45 protein (e.g., a recombinant GADD45) to immunoprecipitated Cdc2/Cyclin B1 complex in vitro leads to the dissociation of this complex. Thus, the invention provides a novel means to identify a composition that binds GADD45 and modulates GADD45 activity by determining its ability to attenuate the GADD45 polypeptide-mediated dissociation of the Cdc2/Cyclin B1 complex. In a variation of this assay, the GADD45 is added in vivo and the components of the Cdc2/Cyclin B1 complex individually isolated (e.g., by immunoprecipitation) to assess whether the complex remains intact or has dissociated.

The invention also for the first time identifies the active site and the protein:protein binding domain of the GADD45 polypeptide, including the domain responsible for GADD45 binding to the Cdc2 polypeptide. The presence of the protein:protein binding domain is necessary for GADD45 to bind Cdc2 and dissociate the Cdc2/cyclin B1 complex to inhibit its kinase activity. Without sufficient Cdc2/cyclin B1 complex kinase activity, the cell cycle arrests at the G2/M checkpoint (which occurs when intracellular GADD45 levels increase, as after a cell's exposure to a DNA base-damaging agent). Based on tests using GADD45 deletion mutants, the binding domain is localized within the region between GADD45 amino acid residues 50–76 of SEQ ID NO:2.

Based on these GADD45 polypeptide deletion analyses and sequence identity (homology) analyses of human GADD45 and other GADD45-related polypeptides (see, e.g., Takekawa (1998) Cell 95:521–530), an active site has been determined to be between residues 61 and 87 (of SEQ ID NO:2). More specifically, residues 62–67 have been determined by mutation analysis to be especially important to the ability of GADD45 to inhibit the phosphorylation of histone H1 by a Cdc2/cyclin B1 complex. Thus, by providing inhibitors of GADD45 that target this domain in the polypeptide, the invention provides novel means to inhibit GADD45 polypeptide activity and sensitize a cell to a DNA damaging agent.

Specifically, the invention provides new inhibitors of GADD45 activity in the form of GADD45 peptides comprising "active site" sequences. These GADD45 "active site" peptides interact with sites which are important to GADD45 interactions with other polypeptides, e.g., Cdc2, to interfere with the activity of endogenous GADD45 polypeptide. These "active site" peptides comprise the acidic motif DEDDDR (SEQ ID NO:5) found at residues 62–67 of GADD45 (SEQ ID NO:2), and modified forms of this sequence, and portions of the GADD45 sequence which flank this motif. The "active site" peptides can be subsequences of a GADD45 binding site domain, e.g., in various embodiments, they are 10, 20, 30, 40, 50, and 60 amino acid residues in length. It should be noted that residues 62–67 are involved in GADD45-Cdc2 binding interactions, but are not solely responsible for these interactions. Binding interactions are localized in the domain defined by residues 50–76 of SEQ ID NO:2.

The invention demonstrates that the acidic motif DEDDDR (SEQ ID NO:5) is important in native GADD45 for GADD45-induced G2/M arrest. The acidic nature of this region is conserved among the GADD45 family, including GADD45β and GADD45γ. Acidic regions of these other members of the GADD45 family, however, do not have the ability to block GADD45-induced G2/M arrest.

The ability of GADD45 peptides to inhibit GADD45-related G2/M arrest can be tested with a "scramble" negative control peptide of the same composition. Peptides are synthesized and purified by HPLC to greater than 90% purity. These GADD45 "active site" peptides are analyzed in in vitro and in vivo assays, e.g., for their ability to bind to Cdc2; inhibit Cdc2/Cyclin B1 kinase activity; block GADD45 binding to Cdc2; and to block GADD45-mediated attenuation of cell growth arrest and apoptosis after exposure of cells to DNA damaging agents, as described herein.

Ran, a small nuclear GTPase implicated in both cell cycle progression and nuclear export (Lounsbury, K. M., et al., *J Biol Chem* 271:32834–32841 (1996); Ren, M., et al. *Mol. Cell Biol* 14:4216–4224 (1994)), contains a closely related acidic motif. DEDDDL (SEQ ID NO: 14), in its carboxyl-terminal domain. (Richards, S. A., et al., *J Biol Chem* 270:14405–14411 (1995)). Overexpression of Ran also predominantly induces a G2/M arrest, whereas deletion of this acidic motif abolishes such activity. (Ren, M., et al., *Mol. Cell Biol* 14:4216–4224 (1994).) Ran, however, is present in cells in large amounts and its levels do not seem to be regulated by DNA damage or stress. Thus, the studies regarding the presence of an acidic motif in the Ran protein did not offer any suggestion that the acidic motif of that protein could be used to block G2 arrest in cells undergoing DNA damage or stress.

The findings reported herein suggest that GADD45 and Ran may utilize a similar pathway to regulate cell cycle progression from the G2 phase to mitosis, and this acidic motif may serve as a common structural entity to activate the G2/M checkpoint. The present findings therefore provide the first information permitting exploitation of the acidic motif for inhibiting the growth and proliferation of cancer cells by inactivating the G2/M checkpoint mediated by GADD45. This strategy permits enhancement of cancer chemotherapy, because inactivation of a G2/M checkpoint can sensitize cancer cells to undergo DNA damage-induced apoptosis. (Pizzo, P. A., et al., in V. T. DeVita, Jr., S. Hellman, and S. A. Rosenberg (eds.), *Cancer: Principles & Practice of Oncology*, J.B. Lippincott Co. Philadelphia, pp. 1738–1791 (1993).)

Definitions

Unless otherwise defined, terms used herein have their conventional meaning as understood by persons of skill in the art. The following terms are defined herein to provide additional guidance to one of skill in the practice of the invention.

The term "alkylating agent" as used herein incorporates the terms common usage and includes all alkylating agents capable of damaging DNA base residues. Exemplary base-damaging alkylating agents include methyl-methane sulfonate ("MMS") (see, e.g., Shirahige (1998) *Nature* 395:618–621; Mothersill (1998) *Int. J. Radiat. Biol.* 74:673–680); N-methyl-N'-nitro-N-nitroso-guanidine (MNNG) (see, e.g., Kumari (1998) *Cancer Res* 58:5075–5078; melphalan (see, e.g., Grant (1998) *Cancer Res.* 58:5196–200); nitrogen mustard (see, e.g., Boddie (1998) *Br. J Cancer* 77:1395–1404); cisplatin and carboplatin (see, e.g., Hawkins (1996) *Cancer Research* 56:892–898.

The term "antibody" refers to a peptide or polypeptide substantially encoded by an immunoglobulin gene or immunoglobulin genes, or fragments thereof, capable of specifically binding an epitope, see, e.g. Fundamental Immunology, Third Edition, W. E. Paul, ed., Raven Press, N.Y. (1993); Wilson (1994) *J. Immunol. Methods* 175:267–73; Yarmush (1992) *J. Biochem. Biophys. Methods* 25:85–97. One of skill will appreciate that antibody fragments may be isolated or synthesized de novo either chemically or by utilizing recombinant DNA methodology. The term antibody also includes "chimeric" antibodies either produced by the modification of whole antibodies or those synthesized de novo using recombinant DNA methodologies. Typically, such chimeric antibodies have the epitope binding site generated from an immunized mammal, such as a mouse, with the structural framework from another mammal, e.g., human. Immunoglobulins can also be generated using phage display libraries, and variations thereof, as described below.

The term "Cdc2 protein" as used herein describes a polypeptide involved in cell cycle control, which can specifically complex with a Cyclin B1 polypeptide to form a "Cdc2/Cyclin B1 protein complex" or a "Cdc2/Cyclin B1 complex." Cdc2 complexed to Cyclin B1 has kinase activity that plays a major role in cell-cycle regulation to drive mammalian cells into mitosis, see, e.g., Toyoshima (1998) *EMBO J* 17:2728–2735; Lowe (1998) *Cell* 94:783–793; Fattaey (1997) *Prog Cell Cycle Res* 3:233–240; Kishimoto (1997) *Prog Cell Cycle Res* 3:241–249.

The term "DNA base-damaging agent" as used herein comprises any agent capable of damaging DNA bases, such as, e.g., ultraviolet (UV) radiation or an alkylating agent (defined above). It also includes agents that can cause DNA damage in the form of intrastrand crosslinks and other diadducts, which, like pyrimidine dimers induced by UV irradiation, are repaired primarily by nucleotide excision repair (see, e.g., Friedberg (1995) DNA Repair and mutagenesis, ASM Press, Washington, D.C.). The term does not include DNA strand-breaking agents, such as infrared (IR) irradiation.

The term "chemotherapeutic agent" includes any reagent that is or has the potential to be administered to a cancer patient for therapeutic or palliative reasons that can cause DNA base damage; e.g., cisplatin and carboplatin (see, e.g., Reed (1998) *Cancer Treat Rev* 24:331–344; Muller (1998) *J Exp Med* 188:2033–2045); nitrogen mustards containing piperidine rings (see, e.g., Henderson (1998) *Anticancer Drug Des* 13:749–768), and the like.

The terms "GADD45" and "wild-type GADD45" refer to a polypeptide involved in cell cycle control which, in humans, is encoded by the nucleic acid sequence of SEQ ID NO:1; with an amino acid sequence of SEQ ID NO:2; see, e.g., Zhan (1998) *Mol Cell Biol* 18:2768–2778; Zhan (1996) *DNA Cell Biol* 15:805–815; Hollander (1993) *J Biol Chem* 268:24385–24393.

The term "GADD45 polypeptide activity" includes all normal protein-protein relationships and functions of the GADD45 polypeptide, including, e.g., its ability to bind other polypeptides, such as, e.g., the Cdc2 polypeptide. The term also includes all normal GADD45 polypeptide biological functions, such as, e.g., its ability to dissociate a Cdc2/Cyclin B1 complex and inhibit the complex's histone kinase activity. It also includes GADD45's ability, when expressed in sufficient amounts, to arrest cell growth at the G2/M checkpoint in the cell cycle (as occurs, e.g., after the cell has incurred DNA base damage by a DNA base-damaging agent, such as UV radiation or an alkylating chemical, such as MMS).

The term "inhibitor of GADD45 polypeptide activity" refers to a composition capable of specifically interfering with GADD45 polypeptide-related G2/M arrest. More specifically, it refers to compositions comprising a DEDDDR (SEQ ID NO:5) subsequence, encompasses compounds, such as polypeptides, which comprise that subsequence and portions of the sequence of the GADD45 protein (SEQ ID NO:2) which flank that subsequence, particularly the alanine on the amino-terminal side and some or all of the first 20 residues on the carboxy terminal side of DEDDDR (SEQ ID NO:5). GADD45 inhibitors also include, e.g., antibodies and small molecules which specifically bind to the GADD45 polypeptide and interfere with its binding to or interaction with, a Cdc2/cyclin B1 complex.

The term "inhibit GADD45 polypeptide activity" refers to a decrease or reduction in the ability of GADD45 to inhibit phosphorylation of histone H1 by a Cdc2/cyclin B1 complex. GADD45 polypeptide activity can be inhibited, for example, by interfering with the ability of GADD45 to cause the dissociation of a Cdc2/cyclin B1 complex.

The term "histone H1" as used herein incorporates its common usage; histone H1 is frequently used in a phosphorylation assay to measure cyclin B1/Cdc2 kinase activity, see., e.g., Wang (1996) *J Natl Cancer Inst* 88:956–965; Pan (1993) *J Biol Chem* 268:20443–20451.

The term "modulator of GADD45 polypeptide activity" refers to any synthetic or natural compound or composition that can change in any way a binding property of or a biological activity of a GADD45 polypeptide. A modulator can be an agonist or an antagonist, an inhibitor of activity or an enhancer of activity. A modulator can be, but is not limited to, any organic and inorganic compound; including, e.g., small molecules, peptides, proteins, sugars (mono- and polysaccharides), nucleic acids, fatty acids, and the like.

The term "proliferating cell" as used herein refers to a cell that is progressing, or has the potential to progress through, the cell cycle and divide. The term "sensitizing a proliferating cell to a DNA-damaging agent" means that the "sensitizing act" (e.g., co-administration of an inhibitor of GADD45 with a DNA-damaging agent) results in a cell that is more "sensitive" to the DNA-damaging agent, i.e., less of a DNA damaging anti-cancer agent is needed to kill the cell or prevent or decrease the cell's replicative capacity.

The terms "specific binding" and "specifically binds", as used herein, when referring to a biomolecule (e.g., protein, peptide, nucleic acid, antibody, etc.), refers to a binding reaction which is determinative of the presence of the biomolecule in a heterogeneous population of molecules (e.g., proteins and other biologics, such as cell extracts). Thus, under designated conditions (e.g. immunoassay conditions in the case of an antibody, physiologic conditions for a binding reaction in a cell or cell extract, stringent hybridization conditions in the case of a nucleic acid), the ligand (e.g., test compound) or antibody binds to its particular "target" molecule (e.g., GADD45) and does not bind in a significant amount to other molecules present in the sample. Thus, a compound capable of specifically binding to a GADD45 polypeptide will bind to GADD45 and not bind in a significant amount to other molecules present in the sample.

The term "test compound" refers to any synthetic or natural compound or composition. The term includes all organic and inorganic compounds; including, e.g., small molecules, peptides, proteins, sugars, nucleic acids, fatty acids and the like.

The term "UV radiation" or "ultraviolet irradiation" as used herein incorporates its common usage and includes all wavelengths capable of incurring DNA base damage, e.g., by inducing pyrimidine dimers (as opposed to the chromosomal strand breakage seen with infra-red ("IR") radiation).

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

Amino acids and analogs described herein are usually referred to by the three letter or single letter codes recommended by the IUPAC-IUB Biochemical Nomenclature Commission. Proteins are stated by convention in order from their amino to their carboxy.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The six groups in the following table each contain amino acids that are conservative substitutions for one another:

TABLE

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W. H. Freeman and Company, New York (1984).

The terms "substantially similar" in the context of a peptide indicates that a peptide comprises a sequence with at least 90%, preferably at least 95% sequence identity to the reference sequence over a comparison window of 10–20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

General Methodologies

The methods of the invention can use GADD45-expressing nucleic acids, including expression cassettes and vectors, capable of expressing GADD45 coding sequences to generate recombinant GADD45 polypeptides in vitro and in vivo. Use of recombinant technologies allows production of variations of GADD45, e.g., deletion constructs, domain rearrangements, and mutations (e.g., as those produced and used in the Examples, below, to identify a GADD45 Cdc2 binding domain). The invention also provides recombinant or synthetic GADD45 fusion proteins to be used, e.g., in assays to screen for compositions that bind to GADD45, or, to inhibit GADD45 function.

Nucleic acids for use in this invention, whether RNA, cDNA, genomic DNA, or hybrids thereof, may be isolated from a variety of sources, genetically engineered, and/or expressed recombinantly. Alternatively, these nucleic acids can be chemically synthesized in vitro. Techniques for the manipulation of nucleic acids, such as, e.g., subcloning into expression vectors, labeling probes, sequencing DNA, DNA hybridization are described in the scientific and patent literature, see e.g., Sambrook, ed., MOLECULAR CLONING: A LABORATORY MANUAL (2ND ED.), Vols. 1–3, Cold Spring Harbor Laboratory, (1989) ("Sambrook"); CURRENT PROTOCOLS IN MOLECULAR BIOLOGY, Ausubel, ed. John Wiley & Sons, Inc., New York (1997) ("Ausubel"); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993). Nucleic acids for practicing the methods of the invention can also be generated using various amplification techniques, see, e.g.,. PCR STRATEGIES (1995), ed. Innis, Academic Press, Inc. ("Innis"), NY; Barringer (1990) Gene 89:117; Kwoh (1989) Proc. Natl. Acad. Sci. USA 86:1173; Guatelli (1990) Proc. Natl. Acad. Sci. USA 87:1874; Smith (1997) J. Clin. Microbiol. 35:1477–1491, Burg (1996) Mol. Cell. Probes 10:257–271. See also, e.g., Santucci (1999) Clin Biochem 32:1–8, describing a competitive polymerase chain reaction (PCR) to quantitate GADD45 expression levels in a cell line.

Polypeptides and peptides used to practice the methods of the invention can also be synthesized, whole or in part, using chemical methods well known in the art (see e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. ("Banga")). For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

Nucleic acids and proteins (e.g., GADD45, Cdc2 and Cyclin B1 polypeptides, and various fusion proteins) used to practice the methods of the invention can be detected and quantified by any means known in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, Southern analysis, Northern analysis, Dot-blot analysis, gel electrophoresis (e.g., SDS-PAGE), RT-PCR, quantitative PCR, other nucleic acid or target or signal amplification methods, radiolabeling, scintillation counting, and affinity chromatography.

GADD45 Nucleic Acid and Polypeptide Sequences

The human GADD45 nucleic acid sequences and other nucleic acids used to practice this invention, whether RNA, cDNA, genomic DNA, or hybrids thereof, may be isolated from a variety of sources, genetically engineered, amplified, and/or expressed recombinantly. Nucleic acid and amino acid sequences of human GADD45 are well known in the art, see, e.g., GenBank Accession Nos. AF078078, AF078077, and M60974. See GenBank Accession No. L24498; and Takekawa (1998) Cell 95:521–530; Papathanasiou (1991) Mol. Cell. Biol. 11:1009–1016. The nucleic acid coding sequence (SEQ ID NO: 1 and the amino acid sequence (SEQ ID NO:2) for human GADD45 are:

```
                                                         (SEQ ID NO:1)
5'-ggcagtggct gggaggcagc ggcccaatta gtgtcgtgcg gcccgtggcg aggcgaggtc    61
cggggagcga gcgagcaagc aaggcgggag gggtggccgg agctgcggcg gctggcacag      121
gaggaggagc ccgggcgggc gaggggcggc cggagagcgc cagggcctga gctgccggag      181
```

-continued

```
cggcgcctgt gagtgagtgc agaaagcagg cgcccgcgcg ctagccgtgg caggagcagc      241
ccgcacgccg cgctctctcc ctgggcgacc tgcagtttgc aatatgactt tggaggaatt      301
ctcggctgga gagcagaaga ccgaaaggat ggataaggtg ggggatgccc tggaggaagt      361
gctcagcaaa gccctgagtc agcgcacgat cactgtcggg gtgtacgaag cggccaagct      421
gctcaacgtc gaccccgata acgtggtgtt gtgcctgctg gcggcggacg aggacgacga      481
cagagatgtg gctctgcaga tccacttcac cctgatccag gcgttttgct gcgagaacga      541
catcaacatc ctgcgcgtca gcaacccggg ccggctggcg gagctcctgc tcttggagac      601
cgacgctggc cccgcggcga gcgagggcgc cgagcagccc ccggacctgc actgcgtgct      661
ggtgacgaat ccacattcat ctcaatggaa ggatcctgcc ttaagtcaac ttatttgttt      721
ttgccgggaa agtcgctaca tggatcaatg ggttccagtg attaatctcc ctgaacggtg      781
atggcatctg aatgaaaata actgaaccaa attgcactga agtttttgaa ataccttttgt     841 agttactcaa gcagttactc cctacactga tgcaaggatt acagaaactg atgccaaggg     901
gctgagtgag ttcaactaca tgttctgggg gcccggagat agatgacttt gcagatggaa     961
agaggtgaaa atgaagaagg aagctgtgtt gaaacagaaa aataagtcaa aaggaacaaa    1021
aattacaaag aaccatgcag gaaggaaaac tatgtattaa tttagaatgg ttgagttaca    1081
ttaaaataaa ccaaatatgt taaagtttaa gtgtgcagcc atagtttggg tatttttggt    1141
ttatatgccc tcaagtaaaa gaaaagccga aagggttaat catatttgaa aaccatattt    1201
tattgtattt tgatgagata ttaaattctc aaagttttat tataaattct actaagttat    1261
tttatgacat gaaaagttat ttatgctata aattttttga aacacaatac ctacaataaa    1321
ctggtatgaa taattgcatc att-3'
```

MTLEEFSAGE QKTERMDKVG DALEEVLSKA LSQRTITVGV YEAAKLLNVD PDNVVLCLLA ADEDDDRDVA LQIHFTLIQA FCCENDINIL RVSNPGRLAE LLLLETDAGP AASEGAEQPP DLHCVLVTNP HSSQWKDPAL SQLICFCRES RYM-DQWVPVI NLPER (SEQ ID NO:2).

Inhibitors of GADD45 Activity

The present invention also provides compounds that are inhibitors of GADD45 activity. In cells that have lost the G1 cell cycle checkpoint (as is often true of cancer cells), these compounds prevent the cell from pausing at the G2/M checkpoint to repair DNA damage. If such cells have DNA damage, and go into mitosis they will then often undergo apoptosis. Thus, such compounds can be used as small molecule, dominant negative inhibitors of GADD45 activity to inhibit the proliferation of cancer cells.

The compounds of the invention include peptides from or derived from the GADD45 amino acid sequence, that contain the DEDDDR (SEQ ID NO:5) acidic motif, and which are capable of interfering with the interaction of GADD45 protein and Cdc2, with the ability of GADD45 to dissociate a Cdc2/cyclin B1 complex, or both. The full length amino acid sequence of human wild type GADD45 is shown in SEQ ID NO:2, above. The full-length protein, of course, interacts with Cdc2 and has normal GADD45 activity, and is not within the scope of the invention herein. The polypeptides of the invention are portions of the GADD45 protein or conservative variations thereof which have activity to modulate GADD45 activity as measured by the assays taught herein, but do not themselves have GADD45-like ability to cause dissociation of a Cdc2/cyclin B1 complex, inhibit a Cdc2/cyclin B1 complex from phosphorylating histone H1, or both. In preferred embodiments, the polypeptides reduce or eliminate the ability of GADD45 to reduce the phosphorylation of histone H1 by a Cdc2/cyclin B1 complex.

In preferred forms, the compounds of the invention include the acidic motifs DEDDDR (SEQ ID NO:5) or DEDDDRD (SEQ ID NO: 15) found at positions 62–68 and 62–69, respectively, of the wild-type GADD45 sequence. Peptide compositions of the invention include not only these specific peptide sequences, but also fragments of the GADD45 protein that contain these motifs and which retain the ability to interfere with GADD45-related dissociation of Cdc2/cyclin B1 complexes. The motifs may also have non-essential moieties attached to the peptides. The term "non-essential moieties", as used herein, refers to those chemical moieties that do not prevent the peptide from inhibiting GADD45-related reduction of the phosphorylation of histone H1. In this context, "non-essential moieties" refers to additional residues or substituents that do not significantly alter the biological properties of the peptides, e.g., their ability to compete with GADD45 in interacting with Cdc2 in Cdc2/cyclin B1 complexes. For example, the term "non-essential moieties" includes amino acid sequence extensions at either the amino-terminal or carboxy-terminal end of the-acidic motifs which do not prevent these peptides from inhibiting the interaction of GADD45 and Cdc2.

Where specific peptide subsequences of a larger protein subsequence are demonstrated to have the requisite properties of the protein, it is apparent to those of skill that the addition of amino acids to the critical peptide is non-essential material. They are preferably added in the natural order (native order) in which they are found in GADD45 as depicted in SEQ ID NO:2. The nonessential material can be added to either end or terminus of the given peptide. These peptides have an amino and carboxy terminus to which additional amino acids can be added. Examples of such amino acid sequence extensions include the portions of the naturally occurring amino acid sequence of GADD45 protein depicted in SEQ ID NO:2 on either side of the acidic motifs. Preferably, such amino acid extensions are no longer than about 25 amino acids in length at either that C-terminal or amino terminal end of the motifs, and more preferably are about 20 amino acids in length or shorter. Because amino acid residues 61 to 87 of SEQ ID NO:2 have been shown to be particularly important in inducing G2/M arrest, more preferred forms of the peptides of the invention contain this sequence (which has some 20 residues extending beyond the acidic motif on the carboxy end). Fewer residues beyond the carboxy end of the acidic motif may, however, be used. For example, the carboxy end can be extended 5, 10, or 15 residues beyond the end of the acidic motif. The ability of any such peptides to inhibit GADD45-related dissociation of Cdc2/cyclin B1 complexes can be determined by the methods described herein. Exemplary peptides or polypeptides of the invention include the following:

EAAKLLNVDPDNVVLCLLAADEDDDRDVALQIHFTLIQAFCCENDI; (SEQ ID NO:16)

LLNVDPDNVVLCLLAADEDDDRDVALQIHFTLIQAFCC; (SEQ ID NO:17)

DNVVLCLLAADEDDDRDVALQIHFTL; (SEQ ID NO:18)

CLLAADEDDDRDVALQIHFTL; (SEQ ID NO:19)

DNVVLCLLAADEDDDRDVALQ; (SEQ ID NO:20)

EAAKLLNVDPDNVVLCLLAADEDDDR; (SEQ ID NO:21)

DEDDDRDVALQIHFTLIQAFCCENDI; (SEQ ID NO:22)

ADEDDDRDVALQIHFTLIQAFCCENDI; (SEQ ID NO:23)

ADEDDDRDVALQIHFTL; (SEQ ID NO:24)

ADEDDDRDVALQ; (SEQ ID NO:25)

DEDDDR; (SEQ ID NO:5)

ADEDDDR; (SEQ ID NO:26)

DNVVLCLLAADEDDDR; (SEQ ID NO:27)

CLLAADEDDDR; (SEQ ID NO:28)

CLLAADEDDDRD; (SEQ ID NO:29)

CLLAADEDDDRDVAL; (SEQ ID NO:30)

DNVVLCLLAADEDDDRDVALQIHFTLIQAFCCENDI; and (SEQ ID NO:31)

LNVDPDNVVLCLLAADEDDDRDVALQIHFTLIQAFCCENDI. (SEQ ID NO:32)

The peptides of the invention may also have conservative amino acid substitutions from the sequence depicted in SEQ ID NO:2. The substitution of amino acids having similar chemical properties such as charge or polarity in regions other than the acidic motif are not likely to affect the ability of the peptides to inhibit GADD45-related dissociation of Cdc2/cyclin B1 complexes. Examples include substitutions of asparagine for glutamine or aspartic acid for glutamic acid. Regions outside of the acidic motif are more preferred than are substitutions within the acidic motif. Such substituted polypeptides can be readily tested by, for example, the assays taught below, to ensure that the substituted peptide remains capable of inhibiting GADD45-related reduction in the phosphorylation of histone H1.

The phrase "consisting essentially" in the context of a compound or peptide is meant to comport with the generally accepted legal meaning of such words. That is the compound may include non-essential material that does not material effect the essential nature of the compound. These would include biologically non-functional material but would also include targeting moieties that direct the peptide to particular cells or subcellular components but that to not materially alter the ability of the peptide to bind to its target proteins or to induce apoptosis.

The polypeptides of the invention should inhibit the ability of GADD45 to reduce phosphorylation of histone H1 by at least 10%. In more preferred forms, the polypeptides of the invention can inhibit such GADD45-related reduction of phosphorylation by 20%, 25%, 33⅓% 40%, 50%, 60% or 75%. In even more preferred forms, the polypeptides inhibit reduction of phosphorylation of histone H1 by 80%, 85%, 90%, 95%, or even more.

Peptides of the invention can be-used in a variety of in vitro applications. For example, in some therapeutic regimens, cells are removed from a patient and expanded in culture before being returned to the patient. Such cells can be contacted with peptides of the invention to preferentially sensitize any cancer cells which might be present to chemotherapeutic agents. The culture is then contacted with a chemotherapeutic agent, or UV radiation, at a level which kills the sensitized cancerous cells, but which does not kill the non-cancerous cells. If a chemotherapeutic agent has been used, the medium is then changed to remove the chemotherapeutic agent, and the non-cancerous cells are then expanded by normal protocols and returned to the patient. Like procedures can be applied to cells maintained in cell cultures to "purge" the cultures of any cancer cells which may be present.

The peptides of the invention can also be used in a variety of in vivo applications. Typically, the peptides will be administered to inhibit the growth or proliferation of cancer cells by sensitizing them to DNA-damaging agents, such as chemotherapeutics.

The peptides of the invention can be delivered to target cells by nucleic acids encoding the peptides. Typically, the nucleic acids will be operably linked to a suitable promoter. In in vivo uses, if a tumor or other site of cells of interest are accessible to a surface, the nucleic acids can be delivered directly to the cells, by a GeneGun or one of the other means known in the art for delivering so-called "naked" DNA. Where parenteral administration is desired or where the cells of interest are not accessible for direct delivery of a nucleic acid encoding the peptides, the nucleic acids can be delivered by other means known in the art, such as by loading the nucleic acids into a liposome, which may be targeted to the cells of interest with appropriate ligands.

Anti-GADD45 Antibodies

The methods of the invention use anti-GADD45 polyclonal and monoclonal antibodies directed against GADD45 polypeptides and peptides, particularly those directed against portions of SEQ ID NO:2 which are involved GADD45 activity, such as amino acid residues 62–68 (the DEDDDR (SEQ ID NO:5) acidic motif) and against portion of GADD45 involved in protein:protein binding with Cdc2, such as those defined by the region between amino acid residues 50–76 of SEQ ID NO:2.

Antibodies can also be used to isolate GADD45 polypeptides. Antibodies are also used in various assays to determine whether a composition is a modulator of GADD45 activity, as described below. Anti-GADD45 antibodies can also used directly as inhibitors of GADD45 polypeptide activity. Generation of polyclonal and monoclonal antibodies, and recombinant (e.g., phage display) libraries reactive with GADD45 are well known to those of skill in the art and described in the scientific and patent literature, see, e.g., Coligan, CURRENT PROTOCOLS IN IMMUNOLOGY, Wiley/Greene, N.Y. (1991); Stites (eds.) BASIC AND CLINICAL IMMUNOLOGY (7th ed.) Lange Medical Publications, Los Altos, Calif.; Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York.

Such techniques include selection of GADD45 reactive antibodies from libraries of recombinant antibodies displayed on phage ("phage display libraries") or on cells. See, e.g., Huse (1989) Science 246:1275; Ward (1989) Nature 341:544; Hoogenboom (1997) Trends Biotechnol. 15:62–70; Katz (1997) Annu. Rev. Biophys. Biomol. Struct. 26:27–45. Recombinant antibodies can also be expressed by transient or stable expression vectors in mammalian cells, as in Norderhaug (1997) J. Immunol. Methods 204:77–87; Boder (1997) Nat. Biotechnol. 15:553–557.

Specific monoclonal and polyclonal antibodies and antisera will usually bind with a $K_D$ of at least about 1 µM, preferably at least about 0.1 µM or better, and most preferably, 0.01 µM or better.

Fusion Proteins

Peptides and polypeptides used to practice the invention (e.g., GADD45, Cdc2) can also be synthesized and expressed as fusion proteins with one or more additional domains linked thereto for, e.g., producing a more immunogenic peptide, to more readily isolate a recombinantly synthesized peptide, attachment to a fixed substrate for column chromatography and high throughput screening analysis (described below), and the like. Detection, substrate attachment and purification facilitating domains include, e.g., metal chelating peptides such as polyhistidine tracts and histidine-tryptophan modules that allow attachment and/or purification on immobilized metals, protein A domains that allow attachment and/or purification on immobilized immunoglobulin, and the domain utilized in the FLAGS extension/affinity purification system (Immunex Corp, Seattle Wash.).

The inclusion of a cleavable linker sequences such as Factor Xa or enterokinase (Invitrogen, San Diego Calif.) between the attachment/ purification domain and the GADD45 peptide or polypeptide can be useful to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–14). The histidine residues facilitate detection and purification while the enterokinase cleavage site provides a means for purifying the GADD45 polypeptide from the remainder of the fusion protein. Technology pertaining to vectors encoding fusion proteins and application of fusion proteins are well described in the scientific and patent literature, see e.g., Kroll (1993) DNA Cell. Biol., 12:441–53.

Screening for GADD45 Polypeptide Binding Activity

The invention provides in vitro and in vivo methods of assaying for a modulator of GADD45 polypeptide activity by identifying molecules that specifically bind the GADD45 polypeptide, thereby affecting its activity. While the invention is not limited by what means the GADD45 polypeptide activity is inhibited, specific embodiments include assaying for GADD45 polypeptide binding to Cdc2, its ability to dissociate a Cdc2/Cyclin B1 complex and inhibit the complex's kinase activity, and others, as described herein. One embodiment includes targeting the active site and protein:protein binding domain of the GADD45 polypeptide, which is described for the first time herein, as discussed above. Additionally, the DEDDDR (SEQ ID NO:5) acidic motif can be targeted. The methods of the invention also include screening for antibodies directed to GADD45 or small molecule binders of GADD45 polypeptides. To assay for specific binding of a putative modulatory molecule, the GADD45 polypeptide can be in solution or can be attached to a fixed substrate. In one embodiment, GADD45 polypeptide is fixed to a solid substrate for high throughput screenings and column chromatography.

Antibodies Directed to GADD45

Polyclonal or monoclonal antibodies can be used in vitro or in vivo to inhibit GADD45 activity. In one embodiment, antibodies are directed to active site binding domains on the GADD45 polypeptide, as discussed above.

When used in assays to identify modulators of GADD45 and compositions that bind to the GADD45 polypeptide, antibodies can non-covalently bind GADD45 polypeptides to the solid support. This can be done directly by binding GADD45-specific antibodies directly to the support (e.g., a column) and allowing GADD45 proteins to bind. Alternatively, it can be done by creating protein chimeras constructed from GADD45 linked to an appropriate immunoglobulin constant domain sequence, i.e., "immunoadhesins," see, e.g., Gascoigne (1987) Proc. Natl. Acad. Sci. USA 84:2936–2940; Capon (1989) Nature 377:525–531; Traunecker (1989) Nature 33:68–70.

Attaching of the GADD45 Polypeptide to Solid Supports

Column Chromatography

GADD45 polypeptide, whether full length, or subsequences thereof (e.g., an active domain or protein:protein binding domain) can be bound to a variety of solid supports. Solid supports that can be used in the methods of the invention include membranes (e.g., nitrocellulose or nylon), microtiter dishes (e.g., PVC, polypropylene, or polystyrene), test tubes (glass or plastic), dip sticks (e.g., glass, PVC, polypropylene, polystyrene, latex and the like), microfuge tubes, or glass, silica, plastic, metallic or polymer beads or other substrates such as paper. One solid support uses a nickel column which binds with specificity to a histadine tag engineered onto a recombinant GADD45-polyhistadine fusion protein (see fusion protein discussion, above).

Adhesion of a GADD45 "target" molecule to the solid support can be direct (i.e. directly contacting the solid support) or indirect (a particular compound or compounds are bound to the support and GADD45 binds to this compound rather than the solid support). Immobilization of compounds can be covalent, e.g., utilizing single reactive thiol groups of cysteine residues (see, e.g., Colliuod (1993) *Bioconjugate Chem.* 4:528–536). Alternatively, compounds can be immobilized non-covalently but specifically, e.g., via immobilized antibodies (see above), as described by Schuhmann (1991) *Adv. Mater.* 3:388–391; Lu (1995) *Anal. Chem.* 67:83–87; or, the biotin/strepavidin system, see, e.g., Iwane (1997) *Biophys. Biochem. Res. Comm.* 230:76–80); or metal chelating, e.g., Langmuir-Blodgett films (Ng (1995) *Langmuir* 11:4048–4055; Schmitt (1996) *Angew. Chem. Int. Ed. Engl.* 35:317–20; Frey (1996) *Proc. Natl. Acad. Sci. USA* 93:4937–41; Kubalek (1994) *J. Struct. Biol.* 113: 117–123; or, metal-chelating self-assembled monolayers, see, e.g., Sigal (1996) *Anal. Chem.* 68:490–497, for binding of polyhistidine fusion proteins.

Indirect binding of GADD45 can be achieved using a variety of linkers, many of which are commercially available. The reactive ends can be any of a variety of functionalities, e.g., amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be aliphatic or aromatic. Examples of commercially available homobifunctional cross-linking reagents include, but are not limited to, the imidoesters such as dimethyl adipimidate dihydrochloride (DMA), dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl) aminobenzoate (SIAB) and the sulfosuccinimidyl derivatives such as sulfosuccinimidyl(4-iodoacetyl) aminobenzoate (sulfo-SIAB) (Pierce Chemicals, Rockford, Ill.). Another group of coupling agents is the heterobifunctional and thiol cleavable agents such as N-succinimidyl 3-(2-pyridyidithio)propionate (SPDP) (Pierce).

By manipulating the solid support and the mode of attachment of the target GADD45 molecule to the support, it is possible to control the orientation of the GADD45 polypeptide. Thus, for example, where it is desirable to attach the GADD45 molecule to a surface in a manner that leaves a "tail" (preferably including an active site or a protein:protein binding site) free to interact with other molecules, e.g., a GADD45 fusion protein with a binding domain and a non-GADD45 tag (e.g., FLAG, myc, GST, polyHis, etc.) for attachment to the column.

Once bound there are a variety of assay formats that can be used to screen for modulators of the GADD45 polypeptide. For example, molecules that interact with a GADD45 binding domain can be identified by attaching the GADD45 to a solid support, contacting a second molecule with the support coated with GADD45, and detecting the binding of the second molecule to the GADD45. Molecules that interact or bind with the target are then eluted, thereby isolating molecules that interacted with the GADD45.

Assays

A variety of different assays for detecting compounds and compositions capable of binding GADD45 are used in this invention. For a general description of different formats for binding assays, see BASIC AND CLINICAL IMMUNOLOGY, 7$^{th}$ Ed. (D. Stiles and A. Terr, ed.)(1991); ENZYME IMMUNOASSAY, E. T. Maggio, ed., CRC Press, Boca Raton, Fla. (1980); and "Practice and Theory of Enzyme Immunoassays" in P. Tijssen, LABORATORY TECHNIQUES IN BIOCHEMISTRY AND MOLECULAR BIOLOGY, Elsevier Science Publishers, B.V. Amsterdam (1985).

In competitive binding assays, the test compound competes with a second compound (known to specifically bind GADD45, e.g., Cdc2) for specific binding sites on the GADD45 molecule attached to the solid support. Binding is determined by assessing the amount of second compound associated with the fixed GADD45 molecule. The amount of second compound (e.g., Cdc2) associated with GADD45 is inversely proportional to the ability of a test compound to compete in the binding assay.

The amount of inhibition or stimulation of binding of a labeled second compound by the test compound depends on the binding assay conditions and on the concentrations of labeled analyte and test compounds used. Under specified assay conditions, a test compound is said to be capable of inhibiting the binding of a second compound to a GADD45 target compound if the amount of bound second compound is decreased by 50% or more compared to a control (no test compound) sample.

Alternatively, various known or unknown compounds, including proteins, carbohydrates, and the like, can be assayed for their ability to directly, and specifically, bind to the target immobilized GADD45 polypeptide. In one embodiment, samples from various tissues are contacted with GADD45. In another embodiment, small molecule libraries and high throughput screening methods are used to identify compounds that bind to the target. The GADD45-binding molecules is then eluted using any method, e.g., column chromatography techniques.

Labels

The amount of binding of a putative GADD45-binding compound can be assessed by directly labeling the test compound with a detectable moiety. Alternatively, binding of the test compound can be detected by binding a labeled ligand that specifically binds to the test compound. A wide variety of labels can be used. The detectable labels can be primary labels (where the label comprises an element that is detected or that produces a directly detectable signal) or secondary labels (where the detected label binds to a primary label, e.g., as is common in immunological labeling). An introduction to labels, labeling procedures and detection of labels is found in Polak and Van Noorden (1997) *Introduction to Immunochemistry*, 2$^{nd}$ ed., Springer Verlag, NY and in Haugland (1996) *Handbook of Fluorescent Probes and Research Chemicals,* a combined catalog and handbook published by Molecular Probes, Inc., Eugene, Oreg. Useful primary and secondary labels can include spectral labels such as fluorescein isothiocyanate (FITC) and Oregon Green™, rhodamine and derivatives (e.g. Texas red, tetrarhodimine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C or $^{32}$P), enzymes (e.g. horseradish peroxidase, alkaline phosphatase, etc.), spectral colorimetric labels such as colloidal gold and colored glass or plastic (e.g. polysytrene, polypropylene latex, etc.) beads. The choice of label depends on sensitivity required, ease of conjugation with the compound, stability requirements, and available instrumentation.

Typical detectors include spectrophotometers, phototubes and photodiodes, microscopes, scintillation counters, cameras, film and the like, as well as combinations thereof. Examples of suitable detectors are widely available from a variety of commercial sources known to persons of skill.

High-Throughput Screening of Candidate Agents that Bind GADD45 Polypeptide

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one embodiment, high throughput screening methods are used to identify compositions that specifically bind GADD45 polypeptide and modulate its activity. This involves providing a library containing a large number of potential compounds (candidate compounds). Such "combinatorial chemical libraries" are then screened in one or more assays to identify those library members (particular chemical species or subclasses) that bind GADD45. The compounds thus identified can serve as conventional "lead compounds" or can themselves be used as potential or actual reagents.

Combinatorial Chemical Libraries

A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks can result in the theoretical synthesis of 100 million tetrameric compounds or 10 billion pentameric compounds (see, e.g., Gallop (1994) 37:1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37:487–493, Houghton (1991) *Nature,* 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs (1993) *Proc. Nat. Acad. Sci. USA* 90: 6909–6913), vinylogous polypeptides (Hagihara (1992) *J. Amer. Chem. Soc.* 114: 6568), nonpeptidal peptidomimetics with a Beta-D-Glucose scaffolding (Hirschmann (1992) *J. Amer. Chem. Soc.* 114: 9217–9218), analogous organic syntheses of small compound libraries (Chen (1994) *J. Amer. Chem. Soc.* 116: 2661), oligocarbamates (Cho (1993) *Science* 261:1303), and/or peptidyl phosphonates (Campbell (1994) *J. Org. Chem.* 59: 658). See, generally, Gordon (1994) *J. Med. Chem.* 37:1385, nucleic acid libraries, peptide nucleic acid libraries (see, e.g., U.S. Pat. No. 5,539,083) antibody libraries (see, e.g., Vaughn (1996) *Nature Biotechnology* 14:: 309–314), and PCT/US96/10287), carbohydrate libraries (see, e.g., Liang (1996) *Science* 274:1520–1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514).

Devices for the preparation of combinatorial libraries are commercially available; see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.; the Ultra-high Throughput Screening System (UHTSS™) capable of screening over 100,000 compounds per day, Aurora Biosciences, San Diego, Calif.

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.).

High throughput Assays of Chemical Libraries

Any of the assays for compounds capable of binding GADD45 polypeptide and/or modulating GADD45 activity described herein are amenable to high throughput screening. These systems (examples of which as described, above) can automate entire procedures including all sample and reagent pipetting, liquid dispensing, timed incubations, and final readings of the microplate in detector(s) appropriate for the assay. These configurable systems provide high thruput and rapid start up as well as a high degree of flexibility and customization.

Assays to Identify Modulators of GADD45 Activity

The invention provides methods of assaying for modulators of GADD45 polypeptide activity. Any means can be used to determine if a composition activates or inhibits GADD45 activity, including in vitro and in vivo assays. All of these assays (particularly the in vitro assays) can be designed for high throughput assay methodologies, as described above. While the invention is not limited by what means a composition inhibits or activates GADD45 activity or by what assay this modulation is determined, several exemplary means are described below.

Inhibition of GADD45 Effects on Cdc2/Cyclin B1 Complex Activity in Vitro

Recombinant GADD45 can strongly inhibit the kinase activity of the Cdc2/Cyclin B1 complex. One exemplary assay is the histone H1 kinase activity assay. The ability of a Cdc2/Cyclin B1 complex to phosphorylate proteins, particularly histone proteins, such as histone H1, can be determined in vitro or in vivo (see below). In in vitro assays, isolated Cdc2/Cyclin B1 complexes are used. This assay is a particularly effective means to determine if a composition is modulator, e.g., an inhibitor, of GADD45 polypeptide activity. As with other assays described herein, it can be adapted to column chromatography or any high throughput methodology. See., e.g., Wang (1996) *J Natl Cancer Inst* 88:956–965; Pan (1993) *J Biol Chem* 268:20443–20451. An exemplary means to measure GADD45's ability to inhibit the kinase activity of isolated Cdc2/Cyclin B1 complexes is provided in the Examples, below.

Inhibition of GADD45 Binding to Cdc2 in Vitro

The invention also provides means to identify modulators of GADD45 activity by measuring the test compound's ability to inhibit GADD45 polypeptide specific binding to Cdc2 polypeptide. For example, using an ELISA assay, the binding of recombinant GADD45 to isolated Cdc2 can be measured in vitro, as described in the Examples, below. Variations of this assay are particularly well suited for column chromatography and high throughput methodologies. For example, the GADD45 and/or the Cdc2 can be fixed to solid supports, labeled, be used as recombinant fusion proteins (to aid in rapid isolation or detection), and the like.

Inhibition of GADD45 Binding to Cdc2 in Vivo

A test compound's ability to inhibit GADD45 polypeptide specific binding to Cdc2 polypeptide can also be determined in vivo. For example, tagged, recombinant GADD45 can be used to measure its association with Cdc2 in tissue culture cells, in vivo; an exemplary means for such an analysis is described in the Example, below.

Inhibition of GADD45 Ability to Dissociate Cdc2 from Cyclin B1 in Vivo

GADD45 can also be used to disassociate the Cdc2/Cyclin B1 complexes in tissue culture cells, in vivo, providing the basis for another means to screen for modulators of GADD45 polypeptide activity. Test compounds can be co-administered to cells with isolated, synthetic or recombinant GADD45 polypeptide. Alternatively, the GADD45 polypeptide can be expressed in vivo by use of recombinant expression systems. Cdc2, GADD45 and Cyclin B1 polypeptides can be individually isolated by immunoprecipitation (i.e., use of antibodies specific for Cdc2, GADD45 or Cyclin B1 which do not interfere with their binding capabilities). The immunoprecipitated proteins, and protein complexes, can be analyzed by, e.g., chromatography (e.g., SDS-PAGE). For example, if a test compound is an effective inhibitor of GADD45 binding to Cdc2, immunoprecipitation of Cdc2 followed by its analysis under the appropriate non-dissociating conditions would reveal intact Cdc2/Cyclin B1 complexes which, under similar conditions but for the presence of the test compound, would be dissociated. The ability of the test compound to specifically bind GADD45 can be then be determined, as described herein.

Inhibition of GADD45-Mediated Attenuation of Cdc2/Cyclin B1 Kinase Activity after Inducing DNA Damage in Cells in Vivo Normally, after a cell has sustained DNA damage, such as by UV irradiation or exposure to an DNA base alkylating agent, increases in GADD45 levels mediate a reduction in in vivo Cdc2/Cyclin B1 histone kinase activity. Levels of histone phosphorylation can be assessed. Inhibition of GADD45 activity will attenuate that inhibition. Thus, a test compound is assessed for its ability to attenuate a cell's decrease in histone phosphorylation level after the cell's exposure to UV irradiation or other DNA damaging agent. If the administration of the test compound results in lower histone phosphorylation, it can be further analyzed for its ability to bind GADD45, dissociate a Cdc2/Cyclin B1 complex, inhibit Cdc2/Cyclin B1 histone kinase activity in vitro, and sensitize a cell to a DNA damaging agent, as described herein. An exemplary assay is described in the Examples, below.

Inhibition of GADD45 Binding to Chromatin

Inhibitors of GADD45 can also be screened by their ability to interfere with GADD45 polypeptide binding to chromatin, see, e.g., Carrier (1999) Mol Cell Biol. 1999 19:1673–1685. This assay is also particularly amenable to in vitro assays and high throughput analyses. GADD45 can also facilitate topoisomerase relaxing and cleavage activity in the presence of core histones, providing another means to test for inhibitor activity (see, e.g., Carrier (1999) Mol Cell Biol 19:1673–1685).

Inhibition of GADD45-Mediated Growth Arrest of Cells at the G2/M Checkpoint

Increased expression of GADD45, by e.g., transduction of cells by GADD45-expressing expression vector, or by inducing DNA damage, will result in cell growth arrest at the G2/M checkpoint boundary. Thus, an inhibitor of GADD45 activity will attenuate this GADD45-mediated cell growth arrest. GADD45-overexpressing cells will display morphologies that resemble cells arrested in an early phase of mitosis. Thus, cell growth arrest at G2/M, and the effectiveness of the GADD45 modulator to inhibit this arrest, can be determined in a variety of ways, including, e.g., MPM2 immunopositivity, 4N DNA content, and centrosome separation.

MPM2 Immunopositivity

GADD45 overexpression will induce a completely "round-up shape" cell morphology with positive staining using the antibody "MPM2," a monoclonal antibody that specifically recognizes certain phosphorylated proteins only present in mitosis (Chen (1995) Oncogene 11:1931–1937). Additionally, GADD45 growth arrested cells, because they are arrested at the G2/M checkpoint, also show extensive incompletely retracted cytoplasm and a partially condensed chromatin with an intact nuclear membrane.

Cellular DNA Content

GADD45 growth arrested cells, because they are arrested at the G2/M checkpoint, will also have a 4N DNA content. An inhibitor of GADD45 activity will attenuate GADD45-mediated G2/M arrest after induction of DNA damage and allow the cells to progress to mitosis. A variety of means can measure the number of cells in a population with a 4N, verus a 2N, DNA content, including staining followed by FACS or microscopic assessment. An exemplary means is described in the Examples, below.

Centrosome Separation

Since the centrosome replicates during the S phase and separates into two functional centrosomes during mitosis, the status of centrosomes can be one of the methods used to determine which stage of the growth cycle the cell is in, or, in the case of cells which are overexpressing GADD45, which stage of the cell cycle they are arrested. This analysis can thus be used to assess whether a test compound is an inhibitor of GADD45 activity. A centrosome-specific antibody SPJ, described by Balczon (1991) Cell Motil. Cytoskeleton 20:121–135, can be used. For example, cells arrested at the G2/M checkpoint, as with GADD45-arrested cells, will have non-separated centrosomes; whereas, under the same conditions but with an inhibitor of GADD45, the cells will have separated centrosomes.

Inhibition of GADD45 Mediated Resistance to Apoptosis After Exposure to UV Irradiation or Base-Damaging Alkylating Agents Human cells with endogenous GADD45 activity are induced to cell cycle arrest at the G2/M checkpoint following exposure to either UV irradiation or DNA base alkylating agents, such as methyl methanesulfonate (MMS) or N-methyl-N'-nitro-N-nitroso-guanidine (MNNG). Inhibition of GADD45 activity will result in a measurably impaired ability to G2/M checkpoint arrest after such exposure. Thus, inhibition of GADD45 activity results in less DNA repair between exposure to the UV radiation and entry into mitosis, with more cells becoming apoptotic. Accordingly, a composition is an inhibitor is GADD45 if its administration sensitizes cells to UV irradiation, i.e., more cells enter apoptosis at a given UV dose with, than without, administration of the putative inhibitor.

A variety of means to determine whether a cell or a cell population is undergoing apoptosis (versus, e.g., necrosis) is known in the art. A few examples include use of Hoechst propidium iodide histograms; Molecular Probes's YO-PRO-1™ dye; phospholipid binding protein analyses, such as Annexin V; terminal deoxynucleotidyl transferase mediated dUTP nick end labeling (TUNEL) assays; mitochondrial probes (e.g., ApoAlert™, Clontech, Palo Alto, Calif.); caspase (e.g., cysteinyl-aspartic acid protease) activity; various protein:protein interactions (e.g., FADD, TRADD), and the like. See, e.g., DeFrancesco (1999) The Scientist 13:17–19.

Administration of GADD45 Inhibitors and GADD45 Peptides

The invention provides modulators (e.g., inhibitors) of GADD45 polypeptide activity and their therapeutic administration. Modulators that can be used therapeutically also include antibodies and small molecules which bind to GADD45 to inhibit its ability to bind Cdc2, or its ability to dissociate a Cdc2/Cyclin B1 complex, or its ability to inhibit Cdc2/cyclin B1 complex phosphorylation of histone H1. In another embodiment, the modulator is a peptide inhibitor of GADD45 activity comprising a GADD45 active site peptide or a protein:protein binding domain peptide (e.g., based on amino acid residues 62–67 or residues 50–76 of SEQ ID NO:2, respectively) which can specifically associate with a GADD45-binding site on another protein (e.g., Cdc2). These compounds include those found by the methods of the invention and peptides and polypeptides, such as DEDDDR (SEQ ID NO:5) or peptides containing a DEDDDR (SEQ ID NO:5) motif, which inhibit GADD45 polypeptide activity. In one embodiment, the peptides, polypeptides and other compositions of the invention are administered with a pharmaceutically acceptable carrier(s) (excipient) to form the pharmacological composition.

Pharmaceutically acceptable carriers and formulations, e.g., for peptides and polypeptides, are known to the skilled artisan and are described in detail in the scientific and patent literature, see e.g., the latest edition of Remington's Pharmaceutical Science, Maack Publishing Company, Easton, Pa. ("Remington's"); Banga; Putney (1998) Nat. Biotechnol. 16:153–157; Patton (1998) Biotechniques 16:141–143; Edwards (1997) Science 276: 1868–1871; Ho, et al., U.S. Pat. No. 5,780,431; Webb, et al., U.S. Pat. No. 5,770,700; and Goulmy, et. al., U.S. Pat. No. 5,770,201.

The compositions used in the methods of the invention can be delivered alone or as pharmaceutical compositions by any means known in the art, e.g., systemically, regionally, or locally; by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any protocol and in a variety of unit dosage forms depending upon the method of administration, whether it is being co-administered with UV irradiation, a chemotherapeutic agent, and the like. Dosages for typical peptide and polypeptide pharmaceutical compositions are well known to those of skill in the art. Such dosages are typically advisorial in nature and are adjusted depending on a variety of factors, e.g., the initial response (e.g., cancer cell sensitization to the DNA damaging agent), the particular therapeutic context (e.g., what cancer and how is it being treated), patient health and the like. The amount of composition or peptide adequate to generate the desired sensitization response is defined as a "therapeutically effective dose." The dosage schedule and amounts effective for this use, i.e., the "dosing regimen," will depend upon a variety of factors, including the stage of the cancer being treated; timing of the co-administration of the sensitizing agent with the irradiation or cancer chemotherapy; the severity of the disease or condition and dosing of DNA damaging agents; the general state of the patient's health; the patient's physical status; age; the pharmaceutical formulation, and the like. The dosage regimen also takes into consideration pharmacokinetics, e.g., the peptide pharmaceutical composition's rate of absorption, bioavailability, metabolism, clearance, and the like, see, e.g., Remington.

Dosages can be determined empirically, e.g, by abatement or amelioration of symptoms, or by objective criteria, e.g., by assessing the sensitization of cancer cells to the DNA damaging treatment upon the co-administration of the GADD45 activity inhibitor; analysis of blood or histopathology specimens (amount of apoptosis in a biopsy), and the like. Thus, the methods and compositions of the invention are co-administered with anti-cancer DNA-damaging therapeutic reagents in amounts sufficient to sensitize the cancer cells to the therapeutic reagents (thus, less of the toxic DNA damaging agent needs to be administered to be effective in killing cancer cells).

It is recognized that the polypeptides and pharmaceutical compositions of this invention, when administered orally, must be protected from digestion. Protection of a peptide pharmaceutical from protease activity is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ or directly into a solid tumor. Actual methods for preparing parenterally administrable compositions will be known or apparent to those skilled in the art and are described in more detail in such publications as Remington's, supra.

The compositions containing the present polypeptides or a cocktail thereof (i.e., with other proteins) can be administered for therapeutic treatments. In therapeutic applications, compositions are administered to a patient suffering from a disease, in an amount sufficient to cure or at least partially arrest the disease and its complications.

The peptides may be targeted and protected by liposomes. The formation of liposomes and their use to deliver therapeutic agents of various types is well known in the art. The use of liposomes that are stable in the circulation are preferred. In some embodiments, the liposomes are sterically stabilized with polyethylene glycol. In some embodiments, the lipsomes may be loaded with nucleic acids encoding the polypeptides of the invention. The nucleic acid can if desired also encode a signal sequence so that the resulting polypeptide is transported to the nucleus.

Liposomes loaded with compositions of the invention can be targeted to cells of interest, such as cells of a particular cancer, by coupling the liposomes to ligands or antibodies that bind to determinants specific to the cells of interest. For example, if the cells of interest bear a particular epitope not usually present on normal cells, an antibody or a fragment thereof which retains antigen recognition can be used to target a liposome to cells bearing that epitope. Liposomes using antibodies or fragments thereof as targeting moieties are known as immunoliposomes, and methods for forming them are well known in the art. Liposomes can also be used to target liposomes to receptors or other targets on cells of interest. For example if the selected target cells are T cells, typical membrane receptor/targets would include CD2 (T11), CD3, CD4 and CD8. If the target cells are B cells, subcellular targets might include CD10 (CALLA antigen), CD19 and CD20. CD45 is a possible target that occurs broadly on lymphoid cells. Those skilled in the art will realize that other ligands may be chosen that bind to receptors expressed on still other types of cells as described above, for example, membrane glycoproteins or ligand or hormone receptors such as epidermal growth factor receptor and the like.

EXAMPLES

The following examples are offered to illustrate, but not to limit, the claimed invention.

Example 1

GADD45 Inhibits Cdc2/Cyclin B1 Histone Kinase Activity and Identification of the Cdc2 Binding Domain in GADD45

The following example details the inhibitory effect of GADD45 on Cdc2 polypeptide, particularly, Cdc2/Cyclin B1 complex, activity in vitro. It also details the first identification of the GADD45 polypeptide Cdc2 binding domain.

To demonstrate that GADD45 affected Cdc2 polypeptide activity, the effect of full length and truncated recombinant GADD45 (rGADD45) polypeptides on isolated Cdc2/Cyclin B1 complexes was studied.

Briefly, to construct rGADD45 polypeptides, internal GADD45 oligonucleotide primers were designed to contain an inframe 5' NdeI site. They were used to amplify the desired regions from a human GADD45 cDNA construct, pHul45B2, as described by Papathanasiou (1991) supra. PCR products were cloned into the pcrII vector using the TA Kit (Invitrogen, San Diego, Calif.) and sequenced prior to sub-cloning into NdeI/XhoI digested pET14b vector. This series of vectors allowed production of histidine tagged bacterial proteins. GADD45 recombinant proteins were expressed and prepared and the histidine tag removed as described by Carrier (1994) J. Biol. Chem. 269:32672–32677.

In one experiment, 100 ng purified Cdc2-cyclin B1 complexes (Upstate Biotechnology, Lake Placid, N.Y.) were incubated with varying amounts of full length rGADD45 or negative control (NAP 1, Tjandra (1998) Curr. Biol. 8:991–1000; Fujii-Nakata (1992) J. Biol. Chem. 267:20980–20986) polypeptides. For full length rGADD45: 0, 10, 20, 50, 100, 200, and 500 ng were used. For the control (NAP1): 0, 100, 200, and 500 ng were used.

Histone H1 kinase assays were then performed. Briefly, purified Cdc2-Cyclin B1 complexes (Upstate Biotechnology, Lake Placid, N.Y.) were incubated with the indicated amounts of rGADD45 or NAP1 proteins for 5 minutes. Histone H1 kinase assays were then performed in the presence of 10 mg of histone H1 (Upstate, Lake Placid, N.Y.), 15 mM MgCl2, 7 mM β-glycerol phosphate, 1.5 mM EGTA, 0.25 mM sodium orthvanadate, 0.25 mM DTT and 10 mCi of [g-32P]ATP in 25 µl. After 15 min at 37° C., the reactions were mixed with an equal amount of standard 2× SDS protein denaturation loading buffer, size-separated on a 12% SDS-PAGE gel, and analyzed by autoradiography.

rGADD45 strongly inhibited the histone H1 kinase activity of purified Cdc2/Cyclin B1 complex. In contrast, NAP-1, a protein of similar size and charge as GADD45, had no appreciable effect (did not inhibit histone phosphorylation).

To identify the domain responsible for inhibition of Cdc2/Cyclin B1 complex kinase activity, two recombinant GADD45 deletion proteins were manufactured and used in this Cdc2/cyclin B1 kinase assay.

rGADD45 proteins were prepared as described by Carrier (1994) supra. The rGADD45 proteins that were manufactured included, in addition to the full-length polypeptide, truncated forms containing the first 124 amino acid residues (designated "GADD45 Δ125–166") or the first 71 amino acid residues (designated "GADD45 Δ72–166") (see sequence and residue notation of SEQ ID NO:2). Histone H1 kinase assays were carried out as described above with o, 50, 100, and 200 ng of: full-length GADD45; both truncated GADD45 forms (GADD45 Δ125–166, and GADD45 Δ72–166); and, for comparative purposes, p21$^{Cip1/Waf1}$ (see, e.g., Alani (1998) Mol. Carcinog. 23:226–33).

GADD45 Δ72–166 (containing amino acid residues 1 to 71) failed to inhibit Cdc2/cyclin B1 complex histone kinase activity while GADD45 Δ125–166 (contains residues 1 to 124) was able to inhibit phosphorylation of histone by complex. The relative activity of the two truncation constructs demonstrates that a required inhibitory domain of GADD45 is specifically localized within the region between amino acid residues 71 and 124 residues.

GADD45 inhibited Cdc2/Cyclin B1 activity at least as strongly as the universal cyclin cdk inhibitor p21$^{Cip1/Waf1}$. 50 ng of full length rGADD45 reduced the activity to less than 40% of control, while the activity with the same amount of p21$^{Cip1/Waf1}$ was only 66% of the control. With larger amounts of either of these two similar size proteins, there was strong inhibition of histone phosphorylation by both rGADD45 and p21$^{Cip1/Waf1}$.

For the histone assays comparing the inhibitory activity of full length and truncated GADD45 constructs, instead of loading samples onto the gel for electrophoretic analysis, 20 ml aliquots were spotted on phosphocellulose paper and then washed three times with 0.75% phosphoric acid. After an acetone rinse, the radioactivity was measured by scintillation counting. The results are the average of three separate experiments.

A monoclonal antibody against cyclin B1 was next used to immunoprecipitate Cdc2/cyclin B1 complex from a lysate of human cells. Antibodies against human Cdc2, c-Myc, and NAP-1 were obtained from Santa Cruz Biotechnology, Santa Cruz, Calif. Antibodies to cyclin B1, cyclin E, Cdk2 (14471A), and p21$^{Cip1/Waf1}$ were obtained from Pharmingen, San Diego, Calif. The human colon carcinoma line RKO was grown in modified Ham's F12 medium supplemented with 10% fetal bovine serum.

For immunoprecipitation, exponentially growing RKO cells were lysed on ice for 30 min in lysis buffer consisting of 50 mM Tris-HCl (pH 7.5), 120 mM NaCl, 1% NP-40, 2 mg/ml of aprotinin, 2 mg/ml of leupeptin and 100 mg/ml of phenylmethylsulfony fluoride. One mg of cellular protein was immunoprecipitated with anti-Cyclin B1 antibody and protein A agarose beads for 4 hr at 4° C. The immunoprecipitates were washed three times with lysis buffer and then loaded onto a SDS-PAGE gel for immunoblot analysis. The presence of Cdc2/Cyclin B1 was confirmed by immunoblotting.

This precipitate containing Cdc2/cyclin B1 complex displayed substantial histone H1 kinase activity (performed as described, above). Addition of rGADD45 resulted in a progressive inhibition of the enzymatic activity of the isolated Cdc2/cyclin B1 complex. In contrast, rGADD45 had no effect on Cdk2/Cyclin E histone H1 kinase activity. The kinase inhibitor staurosporine, which was included as a positive control, blocked nearly all the activity. p21$^{Cip1/Waf1}$ (see above) strongly inhibited Cdk2/Cyclin E. Considering that up to 3600 ng of full length rGADD45 had no effect on Cdk2/Cyclin E, which is a major G1 cyclin, these results indicate that GADD45, unlike p21$^{Cip1/Waf1}$, is not a general inhibitor for cyclin dependent kinases, but rather is more specific for Cdc2.

Example 2

GADD45 Binding to Cdc2 and Cdc2/Cyclin B1 Complexes

The following example details the finding that GADD45 binds to the Cdc2/cyclin B1 complexes by physically associating with the Cdc2 polypeptide.

Using an ELISA assay approach, rGADD45 protein was found to associate with purified Cdc2/Cyclin B1. Immulon II immunoabsorption plates (Dynatech) were coated with 100 ng of Cdc2/Cyclin B1 complexes (Upstate Biotechnology, Lake Placid, N.Y.) in PBS and incubated overnight at 4° C. After rinsing with PBST (PBS with 0.05% Tween-20) and blocking in 5% nonfat milk in PBST, 40 ng of either full length or truncated (both deletion constructs, as described above) rGADD45 protein were added. Following incubation for one hour at room temperature, the plates were washed and an anti-GADD45 antibody (Zymed, San Francisco, Calif.) was added at a 1:1000 dilution in PBST with 0.5% milk (PBSTM). After 1 hr at 25° C., the plates were washed, and HRP-anti-rabbit antibody diluted at 1:1000 in PBS™ was added before final washes and development using the 1-step TMB Solution (Pierce, Rockford, Ill.). Development was halted by the addition of 50 μl of 1M H2SO4, and optical density was measured using a platereader.

Two samples showed significant binding over background level, the sample containing Cdc2, full-length rGADD45, and GADD45 antibody; and the sample containing Cdc2, GADD45 Δ125–166 deletion protein, and GADD45 antibody. In the sample with GADD45 Δ125–166 binding was 77% of that seen with the full-length rGADD45 protein. No appreciable binding was seen with the shorter GADD45 Δ72–166 truncated protein. This result also indicates that the domain defined by the region between amino acid residues 71 to 124 in GADD45 is involved in the interaction of GADD45 with the Cdc2 protein. This is consistent with the observation that the inhibitory domain of GADD45 localized to this region, as discussed above.

An association between rGADD45 and Cdc2 present in cell lysates was also demonstrated. For these experiments, a recombinant glutathione-S-transferase (GST)/GADD45 fusion protein was constructed. The GADD45 insert was PCR amplified from pHul45B2 using the following primers: (SEQ ID NO:3) 5'GGCGGCTCGAGACTTTGGAGGAAT-TCTCGGC 3' and (SEQ ID NO:4) 5'CATCACCGT-TCAGGGAGATTAATC 3'. Products were cloned into a pcrII vector using the TA cloning kit (Invitrogen, San Diego, Calif.). A representative clone was confirmed by sequencing. The selected insert was removed by XhoI and NotI digestion, gel purified using the Wizard DNA Purification Kit (Promega, Madison, Wis.), and ligated into the XhoI/ NotI digested pGEX4T vector (Pharmacia, Piscataway, N.J.). GST-GADD45 fusion protein induction was prepared from freshly transformed BL21 bacterial cells (Novagen). 150 ml of overnight culture was diluted into 1L of LB with ampicillin and grown at 37° C. to late growth phase (OD600 was approximately 0.8). Cultures were allowed to cool to 28°, before induction with 0.5 mM IPTG for 2 hrs at 28° C. Cultures were spun down, resuspended in PBS+0.1% NP-40, lysed by sonication, passed through a 0.45 mm syringe filter and cleared by centrifugation. The supernatant was passed over a column of glutathione-conjugated Sepharose beads (Pharmacia) and were washed with PBS containing 0.1% NP-40. The Sepharose beads were suspended in an equal volume of the same solution and stored in aliquots at −70° C.

To detect binding of cellular Cdc2 to GST-tagged GADD45, 100 ng of GST or GST-GADD45 fusion protein were incubated with one mg of RKO cellular protein for 4 hr at 40° C. Complexes were then washed three times with lysis buffer and loaded onto a 12% SDS-PAGE gel. Following electrophoresis, the proteins were electrophoretically transferred to Immobin membranes (Millipore, Bedford, Mass.). The membranes were blocked for 30 min in 5% nonfat milk and then incubated with anti-Cdc2 (Santa Cruz Biotechnology, Santa Cruz, Calif.) and anti-cyclin B1 (Pharmingen, San Diego, Calif.) monoclonal mouse antibodies. Antibody was detected by a chemiluminescence system in accordance with the instructions of the manufacturer (Amersham, Buckinghamshire, England)

GST-GADD45 fusion protein or GST alone, which were linked to Sepharose beads, were incubated with cellular lysates, isolated, and analyzed by immunoblotting, as described above. With this approach GST-GADD45 was found to associate with cellular Cdc2, whereas no Cdc2 was detected with GST alone. GST-GADD45 did not associate with cyclin B1, which could indicate that GADD45 only associates with free Cdc2 or displaces Cyclin B1 from Cdc2/Cyclin B1 complexes. No association with Cdk2 was detected in the same experiments using an antibody to Cdk2 (Pharmingen, San Diego, Calif.) instead of Cdc2.

In order to determine if GADD45 associates with Cdc2 in vivo, RKO cells were transfected with Myc-epitope-tagged expression vectors. To construct the Myc-tag-GADD45 expression vector, internal GADD45 primers were designed to contain an in-frame 5' NdeI site and were used to amplify the desired regions from a human GADD45 cDNA construct. PCR products were cloned into the pcrII vector using the TA Kit (Invitrogen, Carlsbad, Calif.) and sequenced prior to subcloning into XhoI/XbaI cut pCS2MT. This allowed expression of the GADD45 constructs tagged with 6 copies of the Myc epitope recognized by the monoclonal 9E10 antibody at the amino-terminus (Rupp (1994) Genes Dev. 8:1311–1323; Turner (1994) Genes Dev. 8:1434–1447).

For mammalian cell transfection, $10^6$ RKO cells were seeded onto 100 mm plates the day before transfection. For each plate to be transfected, 5 mg of DNA and 14 µl of Lipofectamine (Gibco-BRL) were each diluted in 300 µl of Opti-Mem (Gibco-BRL) in separate tubes. Solutions were mixed with vortexing, allowed to sit 10–15 minutes at room temperature, diluted with 2.4 ml Opti-Mem and added to the plate for 5 hours. An equal volume of media with 10% FCS was added and plates were left overnight. Fresh media was added the following day and cells were harvested 48 hrs later.

Lysates from cells expressing Myc-tag-GADD45 fusion protein or unfused Myc-tag were immunoprecipitated with antibodies to c-myc and Cdc2 (both from Santa Cruz Biotech.). Antibodies to Cdk2 (Pharmingen) or Notch (an unrelated human protein) (Santa Cruz), and mouse IgG were included as negative controls. Following immunoblot analysis, the Myc-tagged GADD45 protein was detected in both the cell lysate and after immunoprecipitation with anti-Myc antibody. This indicates that there was appreciable expression of this fusion protein. After immunoprecipitation with Cdc2 antibody, Myc-tagged GADD45 was also detected. No GADD45 was detected with (i.e., was co-immunoprecipitated by) the control antibodies. Similar results were also observed using MCF-7 cells in place of RKO cells. These results were also confirmed with a GST-GADD45 expression vector in place of the Myc-tag/GADD45 expression vector. These results indicate that GADD45 is able to associate with Cdc2 both in vitro and in vivo.

Example 3

GADD45 Dissociates Cdc2/Cyclin B1 Complexes in Vivo

The following example details the finding that GADD45 can dissociate the Cdc2/Cyclin B1 complex.

Since GADD45 inhibited Cdc2/Cyclin B1 activity, but only associated with Cdc2, the possibility was considered that GADD45 acts by dissociating this complex. To test this, anti-Cyclin B1 antibody was used to precipitate cellular Cdc2/cyclin B1 complexes (as above). A "wash off assay" was then carried out in the presence of GADD45. Briefly, RKO cellular protein was immunoprecipitated with anti-Cyclin B1 antibody. The immunoprecipitates were washed 3 times with lysis buffer and twice with 10 mM Tris-HCl (pH 7.5), 10 mM Mg Cl$_2$. Samples were then suspended in 30 ml of 10 mM Tris-HCl (pH 7.5), 10 mM MgCl$_2$. Various amounts of rGADD45 (0, 50, 100, 200, 500 ng) or NAP1 (0, 200, 500 ng) was added to the Cdc2/Cyclin B1 immunocomplexes and incubated for 15 min at 25° C. Following incubation, immunoprecipitates were washed twice with lysis buffer, loaded onto SDS-PAGE gel for electrophoresis, and the membrane was immunoblotted with monoclonal Cdc2 antibody for the detection of Cdc2 protein. Prior to the final immunoprecipitation, an aliquot of the solution was analyzed by immunoblotting with an anti-Cyclin B1 antibody to confirm uniform loading. The expectation was that if GADD45 protein was able to disrupt Cdc2/Cyclin B1 complex, then the second rinse should remove dissociated Cdc2 protein from the Cyclin B/anti-Cyclin-B1 antibody immune complexes. In fact, increasing amounts of GADD45 did reduce the Cdc2 level in these immune complexes. The NAP-1 control had no effect. To confirm uniform levels of Cyclin B1, the amount of Cyclin B1 was measured by immunoblotting. These data demonstrate that GADD45 was able to dissociate Cdc2/Cyclin B1 complexes in vitro in a dose dependent manner.

Example 4

Inhibition of GADD45 Expression Attenuates (GADD45-Mediated) Downregulation of Cdc2/Cyclin B1 Activity The following example details the finding that an inhibitor of GADD45 activity attenuates GADD45-mediated inhibition of Cdc2/Cyclin B1 complex activity (particularly, the complex's ability to phosphorylate histone H1). Significantly, the inhibitor was able to attenuate UV irradiation-stimulated GADD45-mediated inhibition of Cdc2/Cyclin B1 complex activity.

To explore the effect of GADD45 on Cdc2/cyclin B1 in vivo, Cdc2 kinase activity was examined in human p53 wild type (wt) RKO cells and several recombinant sublines altered to express high levels of antisense, activity-inhibiting, GADD45 RNA. In particular, the amount of Cdc2/Cyclin B1 complex activity was measured in cells that had been treated with UV irradiation (which increases GADD45 levels, decreasing kinase activity) in both wild type and recombinantly altered (GADD45-activity negative) cell lines. For UV irradiation, 150-mm dishes were rinsed with PBS and irradiated with germicidal lamps at a dose rate of 2.1 Jm-2/s at 254 nm. The original medium was replaced and the cells were returned to 37° C. for 4 hours. The cells were then harvested for the preparation of cellular protein.

These antisense lines have been shown previously to have more than a 5-fold reduction in GADD45 expression compared to the parental line, and increased GADD45 expression following induction by UV radiation was completely blocked (Smith (1996) Mutation Res. 340:109–124; Smith (1996) Oncogene 13:2255–2263). The growth rate of these lines was equivalent and all (parental and GADD45 activity inhibited) showed a similar G1 arrest after infrared irradiation (IR).

The levels of Cdc2/Cyclin B1 kinase activity (measured as above) were similar in unirradiated cells. Following UV irradiation the parental line, as expected, showed a strong reduction in Cdc2 kinase activity (in response to increases in GADD45 levels). However, this inhibition (of kinase activity) was significantly attenuated in all the antisense (GADD45 activity-inhibited) sublines. These data demonstrate that an inhibitor of GADD45 activity can sensitize a cell to UV irradiation. This result correlates with the attenuated G2/M checkpoint activation after UV radiation, described below.

Example 5

Inhibition of GADD45 "Sensitizes" Cells to Base Damage by Attenuating G2/M Checkpoint Activation and Resistance to Apoptosis The following example details both genetic and functional evidence of a GADD45-mediated G2-M checkpoint in human and murine cells. Increased expression of GADD45 via microinjection of a GADD45-expressing vector into primary human fibroblasts arrests the cells at the G2-M boundary. These cells have a phenotype of MPM2 immunopositivity, 4N DNA content and, in 15% of the cells, centrosome separation. The GADD45-mediated G2/M arrest is dependent on wild-type p53, because no arrest was observed either in p53-null Li-Fraumeni fibroblasts or in normal fibroblasts co-expressed with p53 mutants. Increased expression of cyclin B1 and Cdc25C inhibited the GADD45-mediated G2/M arrest in human fibroblasts, indicating that the mechanism of GADD45-mediated G2-M checkpoint is at least in part through modulation of the activity of the G2-specific kinase, cyclin B1/p34$^{cdc2}$.

Genetic and physiological evidence of a GADD45-mediated G2-M checkpoint was also obtained using GADD45-deficient human or murine cells. Human cells with endogenous GADD45 expression reduced by antisense GADD45 expression have an impaired G2-M checkpoint following exposure to either ultraviolet (UV) radiation or the DNA base-damaging alkylating agent methyl methanesulfonate (MMS). However, these cells are still able to undergo G2 arrest following ionizing radiation.

Furthermore, lymphocytes from gadd45-knockout mice (gadd45−/−) also retained a G2-M checkpoint initiated by ionizing radiation. However, these gadd45-knockout mice also failed to arrest at G2/M following exposure to UV irradiation (as did the GADD45 activity inhibited cells).

GADD45 Arrests Normal Human Fibroblasts at the G2-M Boundary.

To demonstrate GADD45 effect on the cell cycle, normal primary human fibroblasts were microinjected with a GADD45 expression vector. Briefly, primary human fibroblast lines were GM07532, GM00038 and GM03395, from Coriell Cell Repositories, Camden, N.J. A spontaneously immortal LFS041 fibroblast cell line with homozygous deletion of wild-type p53 was derived from a Li-Fraumeni patient as described by Yin (1992) Cell 70:937–948. These cells were grown in Ham's F10 medium supplemented with 15% fetal bovine serum (FBS). Only early passaged primary human cells (before passage nine) were used in experiments. A colon carcinoma cell line HCT-116 contains a functional p53 and p21, and HCT-116(−/−) cells have a homozygous deletion of the p21 gene (Waldman (1996) Nature 381: 713–716). These cells were grown in McCoy's 5A medium with 10% FBS. The HCT-116-E6 cell line was derived from HCT-116 transfected with HPV-16 E6 gene, and this cell line has undetectable p53 protein. The colon carcinoma cell line RKO and its derivative RKO-E6 cells was described by Kastan (1991) Cancer Res. 51:6304–6311. All cells were maintained in the appropriate media at 37° C. in a humidified atmosphere containing 5% $CO_2$.

Regarding the recombinant constructs used in these experiments: p53-143ala and p53-249ser encode missense mutants of human p53, Val 143Ala and Arg249Ser, respectively, described by Wang (1996) supra. pCMV45 encodes a human GADD45 cDNA, described by Zhan (1994) Mol. Cell Biol. 14:2361–2371). pcDNA-cycB1 encodes a 1.6 kb fragment of the human cyclin B1 cDNA. pcDNA-cdc25A, -cdc25B, and -cdc25C encode the human cdc25A, cdc25B and cdc25C cDNA, respectively. These genes are under the control of the cytomegalovirus (CMV) early promoter pactβgal encodes a β-galactosidase gene under the control of chicken β-actin promoter (Miura (1993) Cell 75:653–660). pGreen-Lantern (GFP) was obtained from Gibco/BRL (Gaithersburg, Md.).

The vector microinjection procedure was done as described by Wang (1996) Genes Dev. 10:1219–1232. Plasmid cDNA at a concentration of 100–200 μg/ml was used for microinjection, which results in an average of 10 to 20 molecules per cell. All the microinjected plasmids were purified by a double CsCl centrifugation protocol. At least 50 positive cells were analyzed for each experiment. Data were obtained from at least three independent microinjection experiments. Control plasmids include pactβgal and GFP (see, e.g., Vicini (1998) J Neurophysiol. 79:555–566).

Microinjection of normal primary human fibroblasts with a GADD45 expression vector revealed that overexpression of rGADD45 induces a G2/M arrest. Increased expression of rGADD45 was detected as early as three hours following microinjection of the GADD45 expression vector. Twenty-four hours following microinjection, 44±9% (mean±S.D.) of the GADD45-overexpressing cells displayed morphologies that resemble cells arrested in an early phase of mitosis. These morphologies include a completely round-up shape and with positive staining using the antibody "MPM2," a monoclonal antibody that specifically recognizes certain phosphorylated proteins only present in mitosis (Chen (1995) supra). These cells also showed extensive incompletely retracted cytoplasm and a partially condensed chromatin with an intact nuclear membrane. Nuclei were stained with 4',6-diamidino-2-phenylindole (DAPI).

As noted above, since the centrosome replicates during the S phase and separates into two functional centrosomes during mitosis, the presence of non-separated centromeres is one indication of growth arrest at the G2/M checkpoint. The status of centrosomes (by visualizing the centrosomes) in the GADD45-arrested cells was determined by the centrosome-specific antibody (antiserum) SPJ (Balczon (1991) supra). Approximately 85% of the GADD45-arrested cells contained non-separated centrosomes, as analyzed by immunocytochemistry and confocal microscopy. The remaining 15% of the arrest cells showed two separate centrosomes.

These data indicate that the cells were arrested in early prophase. Similar results were also obtained using normal primary human fibroblasts from a different donor (GM00038). GADD45-associated morphological changes were not observed in cells microinjected only with either β-galactosidase expression vector (β-gal) or GFP expression vector (pGreen-Lantern). GADD45 induction of these morphological changes was not altered by the amount of GADD45 DNA microinjected, which ranged from an average of two molecules GADD45 per cell to forty molecules per cell.

Time-course studies indicate that the fraction of arrested cells increases with the incubation time and reaches to about 83% at 72 hr. Also, all of the cells when entering into the cell cycle appear to be arrested by GADD45 because the numbers of the bromodexoyuridine (BrdU)-labeled cells at the same passages coincide with the numbers of the GADD45-arrested cells.

Cytoplasmic retraction is also associated with GADD45-arrested cells. In the GADD45-arrested cells, retraction eventually went to completion, as confirmed by time-lapse video analysis.

To further demonstrate that the GADD45-arrested cells had passed through S phase, DNA ploidy analysis with a CAS imaging system was performed. Unsynchronized normal primary human fibroblasts displayed a normal log-phase distribution (79% in 2N and 21% in 4N), while virtually all of the cells were 2N after being serum-starved for three days. GADD45-mediated cell cycle-arrested cells displayed 4N DNA contents. For the DNA ploidy analysis, cells were fixed in acetone at −20° C., and quantitatively stained for DNA content by the Feulgen reaction using manufacturer's protocols (Becton Dickinson). Quantitative DNA analysis was performed by the CAS-200 image analyzer (Becton Dickinson). Calibration was performed using the rat hepatocyte. For a quiescent population, fibroblasts were incubated in F10 medium containing 0.1% of FBS for 72 hr. Cells with the GADD45-induced distinct morphology were located and marked under phase contrast microscope prior to CAS image analysis.

Taken together, these data indicate that increased expression of GADD45 in the normal primary human fibroblasts results in a cell cycle arrest at the G2-M transition. Unlike p53 overexpression, increased expression of GADD45 did not lead to the typical morphological changes associated with either p53 or ICE-induced apoptosis (see, e.g., Srinivasan (1996) *J Neurosci* 16:5654–5660; Wang (1996) supra). GADD45 overexpressing cells also were negative by TUNEL assay (see, e.g., Gavrieli (1992) J. Cell Biol. 119: 493–501).

GADD45-Induced Cell Cycle Arrest is p53-Dependent

Although GADD45 induced a G2/M arrest in normal human fibroblasts, it did not induce a G2/M arrest in a fibroblast cell line derived from a Li-Fraumeni patient (LFS041) that does not contain p53 protein (Yin (1992) supra). Overexpression of GADD45 causes a G2/M arrest only in cells with wild type p53, such as the colon carcinoma cell line HCT116, as analyzed by FACS analysis. Furthermore, the dominant-negative p53 mutants can also abrogate a GADD45-induced arrest in normal fibroblasts when co-expressing together, presumably by neutralizing the endogenous wt p53. A protective effect was not observed when GADD45 was co-expressed with either a β-gal expression vector or a GFP expression vector. Thus, GADD45-induced G2/M arrest is p53-dependent.

GADD45 Activity-Inhibited Cells are Defective in DNA Base-Damaging (UV- and MMS)-Induced G2/M Arrest A genetic approach was used to demonstrate that GADD45 is required for the DNA damage-induced cell cycle arrest at the G2-M checkpoint. Using flow cytometry analysis, cell cycle distributions of unsynchronized cell populations were performed (for flow cytometry analysis, cells were harvested with 3.5 mM EDTA-PBS buffer, fixed with 70% ethanol for at least 1 hr at 4° C., treated with 20 μg/ml RNase A for 30 min, stained with 60 μg/ml of propidium iodide (PI) for DNA content, and analyzed for cell cycle status with a FACScan cell sorter (Becton Dickinson). At least 10,000 cells were collected. The cell cycle profiles were calculated using the CellQuest and ModFit Lt software. Experiments were repeated at least twice.) The parental human RKO colon carcinoma cells and three isogenic RKO-derived clones stably expressing antisense GADD45 mRNA (discussed above) were analyzed.

Clones stably expressing antisense GADD45 mRNA have a diminished constitutive GADD45 protein level and are more sensitive to UV radiation, but not to γ-radiation in a clonogenic survival assay (described by, e.g., Smith (1995) Oncogene 10::1053–1059; Smith (1996) Oncogene 13:2255–2263).

Cells were treated with base-damaging agents: either 6.3 Gy of γ-radiation; 5 J/m$^2$ of UV; or, 25 μg/ml of the base-damaging alkylating agent MMS. These doses for MMS and UV radiation were selected because they were not toxic to these cells in a short-term growth assay. Higher doses mainly caused delay in S phase, which may be due to a high frequency of DNA lesions blocking replication or initiating an S-phase checkpoint. The cell cycle status of the cells was then analyzed and quantitated by flow cytometric analysis profile (as described above). The three untreated antisense GADD45 clones had similar G1 fractions, slightly lower S fractions, and slightly increased G2/M fractions, compared to parental RKO cells. IR caused a significant accumulation in G2/M with concomitant reductions in G1 and S in all four cell lines.

Following MMS exposure, the parental RKO cells clearly accumulated in S and G2/M. However, the three GADD45 antisense clones failed to arrest in G2/M following MMS treatment, although the S-phase accumulation still occurred. Similar results were also obtained with cells synchronized by either a uridine biosynthesis inhibitor (phosphoacetyl)-L-aspartate (PALA) or aphidicolin. RKO-E6 cell line also did not accumulate in G2/M after UV or MMS exposure, consistent with the model that p53 may be required for these types of damage-induced G2-M checkpoint.

A BrdU labeling protocol was used to further examine if the lack of a G2/M arrest in GADD45-activity inhibited cells is due to failure in controlling the G2 cell cycle exit. The RKO parental cells and three antisense GADD45-expressing clones were synchronized at the G1-S transition by treatment with 1 μg/ml of aphidicolin for 24 hours. Greater than 95% of cells had a G1 DNA content following synchronization. Upon release from the aphidicolin block, cells were treated with various DNA damaging agents and incubated for an additional 20 hr in the presence of BrdU. Cells were harvested and the BrdU-positive cell populations were subjected to FACScan analysis.

Untreated parental RKO cells and three antisense clones (designated RKOAS45-1, RKOAS45-2, and RKOAS45-14) displayed similar cell cycle distributions: 28%, 30%, 29% and 31% in second G1; 35%,39%, 40% and 39% in first S; 37%,31%, 31% and 30% in first G2/M, respectively. The G1/G2 ratios from parental and RKOAS45-1, RKOAS45-2, RKOAS45-14 were 0.8, 0.9, 1.0 and 1.0, respectively.

Following treatment with 6.3 Gy IR, most of the cells in the parental and antisense clones (greater than 74%) were accumulated in the first G2/M, indicating a functional γ-radiation-induced arrest.

Following exposure to a 5 J/m$^2$ of UV, many of the parental RKO cells (51%) were arrested at the first G2/M, with a small population (22%) in the second G1. However, the three antisense GADD45 expressing clones RKOAS45-1, RKOAS45-2, and RKOAS45-14, did not accumulate at the first G2/M; they continued into the second G1 of the cell cycle. Similar results were obtained when these cells were treated with 25 μg/ml of MMS. Collectively, above data indicate that the parental RKO cells have a physiologically normal G2-M checkpoint in response to UV, MMS and IR treatment. Increased expression of antisense GADD45 mRNA allows the RKO cells to escape the G2/M arrest induced by either UV or MMS treatment (but not by IR).

The mitotic index of lymphocytes derived from normal and gadd45 knockout (−/−) mice in response to UV or IR irradiation was performed. These cells were exposed to either UV radiation at 7.5 J/m$^2$ or to IR at 5 Gy. Briefly describing the mitotic index assay, splenic lymphocytes were isolated from B16/129 mice at 4 to 15 weeks of age. For each experiment, lymphocytes from spleens of 2 or 3 animals, which were littermates, were pooled either from gadd45−/− animals or age-matched wt (gadd45+/+) animals. The genotypes of these cells were verified by Southern blot and PCR-based methods. The cells were grown in RPMI1640 medium (GIBCO-BRL) supplemented with 10% heat-inactivated fetal calf serum, glutamine, and antibiotics. Immediately following harvest, 45 ng/ml 12-O-tetradecanoylphorbol-13-acetate (TPA) (Sigma) and 0.75 μM ionomycin were added; on the following day cells were diluted 2-fold with fresh medium that did not contain additional TPA or ionomycin. Two days after harvest, the suspension cells were centrifuged, transferred to a fresh flask, and suspended in medium containing 40 units/ml of interleukin-2 (IL-2) (Tecin™, Roche) and 50 μM β-mercaptoethanol (Sigma). Cells were diluted daily with medium without cytokines to maintain a density of approximately 10$^6$ per ml and used 1 or 2 days after the addition of IL-2, when they were growing maximally. Under these conditions, the doubling time was approximately 15 hr and the G2/M fraction was approximately 16% by FACS analysis; the mitotic index of unirradiated cells was 2 to 3%, and it was estimated that the duration of G2 was 2 hr or less. For UV irradiation lymphocytes were irradiated with 254 nm germicidal bulbs in 150 mm dishes containing 15 ml of medium. Cells were then incubated at 37° C. for 1 or 2 hr. At each time point cells were harvested and treated with 0.075 M KCl for 12 min at room temperature, fixed in methanol:acetic acid (3:1), spread on a glass microscope slide, air dried, and stained with 5% Giemsa. At least 3,000 cells were counted in each preparation. Data were obtained from three batches of pooled lymphocytes from each collection; data was expressed as the mean ±S.D.

A significant reduction in the percentage of the mitotic cells was observed at both time points in gadd45 +/+ lymphocytes following 7.5 J/m$^2$ of UV treatment, indicating a functional G2-M checkpoint in these cells. However, no alteration of mitotic index in the gadd45−/− lymphocytes exposed to UV radiation was observed. Similar results were observed in lymphocytes exposed to UV radiation at either 7.5 or 2d0 J/m$^2$ from two individual gadd45 mice. However, lymphocytes from gadd45+/+ and gadd45−/− mice displayed normal arrest when irradiated with 5 Gy IR. Taken together, these data demonstrate that cells lacking GADD45 are defective in a G2-M checkpoint induced by DNA base-damaging agents, particularly UV irradiation or MMS.

Cyclin B1 and Cdc25C Attenuate the GADD45-Induced G2/M Arrest

The mechanism(s) of GADD45-mediated G2/M arrest was explored by investigating the effects of G1 to S phase or G2 to M phase by co-expression of GADD45 and other cell cycle-modulating genes. Various cell cycle-related cDNA expression vectors were coinjected with the GADD45 expression vector into normal primary human fibroblasts. Normal primary human fibroblasts were either microinjected alone with GADD45 or co-injected with cyclin B1, cdc25A, cdc25B, cdc25C or p34$^{cdc2}$ (cdc2). Cells were fixed at 24 hr and GADD45-positive cells displaying an arrested morphology were scored. At least three independent microinjection experiments were averaged and data are expressed as mean ±S.D.

Increased expression of either human cyclin B1 or Cdc2 proteins required for the G2-M transition (57), partially blocked the GADD45-induced G2/M arrest (p<0.05). Co-expression of Cyclin B1 and Cdc25C almost completely abolishes GADD45-mediated G2/M arrest. Using Student T-test, a statistically significant p value (<0.05) was obtained between GADD45 alone and coinjection with cyclin B1 and/or Cdc25C. Increased expression of either the human G1-S phase-specific protein phosphatases cdc25A or cdc25B, or the human G2-specific cyclin dependent kinase p34$^{cdc2}$ had little effect on GADD45-induced G2/M arrest.

Because p21 binds to GADD45 in vivo (Chen (1995) supra; Kearsey (1995) Oncogene 11:1675–1683), it was next determined whether p21 is required for the GADD45-mediated G2/M arrest. GADD45 expression vector was microinjected into either HCT116 cells or two clonal derivatives in which the p21 gene was homozygously deleted (see Waldman (1996) Nature 381:713–716). GADD45 was capable of inducing G2/M arrest in all three cell lines. It was also tested whether fibroblasts from patients with ataxia telangiectasia (AT) display an abnormal G2/M arrest by GADD45 (a deficiency in G2-M checkpoint in response to IR treatment has been associated with cells from AT patients (Kastan (1992) Cell 71:587–597; Beamish (1994) Int. J. Radiation Biol. 65:175–184), suggesting that ATM is required for the G2-M checkpoint, similar to RAD3 in *S. pombe* and MEC1 and TEL1 n *S. cerevisiae*). Increased expression of GADD45 efficiently led to a G2/M arrest in fibroblasts from an AT patient (GM03395), a result which is indistinguishable from that seen when GADD45 is overexpressed in normal fibroblasts. Thus, these data demonstrate that both p21 and ATM are dispensable for the GADD45-mediated G2/M arrest in normal human fibroblasts.

CONCLUSION

These findings demonstrate that GADD45 can mediate a G2-M cell cycle checkpoint in both human and murine cells. Genetic evidence of the importance of GADD45 in a G2-M checkpoint is provided by a defective UV but not IR-induced G2/M arrest in gadd45 −/− murine lymphocytes and in antisense GADD45-expressing human colon carcinoma cells. Increased expression of GADD45 in normal primary human fibroblasts arrests the cells in G2/M. The data also agree with the previous reports that antisense GADD45-expressing RKO cells displayed a decreased clonogenic survival to UV radiation but not IR radiation (Smith (1994)

Science 266:1376–1380; Smith (1996) Oncogene 13:2255–2263). Increased expression of GADD45 in normal primary human fibroblasts also arrests the cells at the G2-M transition. The arrested cells show an early mitotic morphology and mitotic markers, with 4N DNA content, a partially condensed nucleus with an intact nuclear membrane, with a delay in cytoplasmic retraction and 15% of the arrested cells have two separated centrosomes. Taken together, these findings demonstrate that GADD45 is required in human cells for a normal G2-M checkpoint in response to DNA base-damaging agents. Furthermore, inhibition of GADD45 activity disables the G2-M checkpoint, which "sensitizes" the cell to the effects of the DNA base-damaging agents, causing the cell to proceed into mitosis with unrepaired DNA damage, thus inducing suicidal apoptosis.

Example 6

Materials and Methods

The following materials and methods were used in the studies discussed in the Examples below.

Plasmids. The open reading frame of the GADD45 cDNA without its own stop codon was directly amplified by PCR and cloned in-frame into pcDNA3-HA, a derivative of pcDNA3 (Invitrogen) modified to include an HA epitope. (Smith, M. L., et al., Science 266:1376–1380 (1994).) GADD45 deletion plasmids were generated by deleting respective regions from pcDNA3-GADD45-HA. The site-mutagenesis plasmids were constructed by a PCR-based approach, followed by ligation in-frame into pcDNA3-HA. GADD45β-HA and GADD45γ-HA vectors were kindly provided by Dr. H. Saito. (Takekawa, M. and H. Saito, Cell 95:521–530 (1998).)

Cell culture, transfections and microinjection. The colon carcinoma cell line HCT116 was cultured in Dulbecco's modified Eagle's medium (DMEM) containing 10% fetal bovine serum (FBS). RKO cells (a colon carcinoma cell line) were maintained in modified Ham's F12 medium containing 10% FBS. COS-7 cells were maintained in DMEM supplemented with 10% FBS. Primary human fibroblasts (GM0842) were obtained from Coriell Cell Repositories (Camden, N.J., USA) and grown in Ham's F10 medium supplemented with 15% FBS. Only early passage primary human cells (before passage 9) were used in the experiments. All cells were maintained at 37° C. in a humidified atmosphere containing 5% $CO_2$. Transfections were performed with Lipofectamine Plus (Gibco/BRL, Gaithersburg, Md.) as directed by the manufacturer. The microinjection procedure used was described previously. (Wang, X. W., et al., Genes Dev. 10:1219–1232 (1996).) Expression vectors at a concentration of 100 μg/ml were used for microinjection, which results in an average of 10 molecules per cell. At least 50 positive cells were analyzed for each experiment. Data were obtained from at least three independent microinjection experiments.

Antibodies. Antibodies against human Cdc2, cyclin B1, $p21^{Waf1}$ and PCNA were obtained from Santa Cruz Biotechnology (Santa Cruz, Calif., USA). Anti-HA antibody was provided by Roth Molecular Biochemicals (IL, USA).

Immunoprecipitation. Cell extracts were prepared on ice for 30 min in lysis buffer containing 50 mM Tris-HCl (pH 7.5), 120 mM NaCl, 1% NP-40, 2 μg/ml of aprotinin, 2 μg/ml of leupeptin and 100 μg/ml of phenylmethylsulfonyl fluoride. Two mg of cellular protein was immunoprecipitated by incubating the extracts with the primary antibodies for 2 h at 4° C., followed by addition of protein A/G agarose beads and incubation for another 2 h at 4° C. with rotation. After five washes in lysis buffer, bound proteins were released by resuspending the beads in 30 μl of Laemmli sample buffer. Proteins were separated by SDS-PAGE and electrophoretically transferred to nitrocellulose membranes (Novex, San Diego, Calif.). Membranes were incubated with anti-HA antibody which was then detected by a chemiluminescence system (Amersham Pharmacia, England).

Immunocytochemistry analysis. Cells were fixed and stained with appropriate antibodies as described previously. (Wang, X. W., et al. Genes Dev. 10:1219–1232 (1996).) Anti-GADD45 or anti-HA antibody was used for staining. Secondary antibodies conjugated to fluorescein isothiocyanate (FITC) or Texas Red (Vector Labs) were used. Nuclei were stained with 4′,6-diamidino-2-phenylindole (DAPI).

Immunocomplex protein kinase assay. A G2-specific kinase assay was done essentially as described (Zhan, Q., et al., Oncogene 18:2892–2900 (1999)) using cellular protein extracts prepared from RKO cells transfected with various GADD45 constructs. Briefly, the Cdc2/cyclin B1 kinase complex was immunoprecipitated from RKO cells with anti-cyclin B1 antibody for 2 h at 4° C. Immunocomplexes were recovered with the aid of protein A agarose beads (Santa Cruz, Calif.), washed three times with lysis buffer and twice with kinase buffer (50 mM Tris-HCl, 10 mM $MgCl_2$, 2 mM DTT, 1 mM EGTA and 0.01% Brij35), and resuspended in 20 μl of kinase buffer containing 1 μg of histone H1 (Upstate, Lake Placid, N.Y.). The histone H1 kinase reaction was initiated by the addition of 10 μCi [$\gamma$-$^{32}$P]ATP and 25 μM ATP with incubation for 15 min at 37° C. Reactions were stopped by addition of an equal volume of 2× Laemmli sample buffer. Histone H1 was separated on a 12% SDS-PAGE gel, which was then dried and visualized by autoradiography.

Cell cycle analysis. RKO cells were trypsined and washed with phosphate-buffered saline, fixed with 70% ethanol overnight at 4° C., treated with 20 μg/ml RNase A for 30 min and stained with 60 μg/ml of propidium iodide (PI) for DNA content. PI fluorescence was analyzed with a FACSCaliber cell sorter (Becton-Dickinson). Data for at least 10,000 cells was collected using CellQuest software (Becton-Dickinson). Cell cycle distributions were calculated using ModFit LT software.

Example 7

Mapping of the Functional Domain of GADD45 Required for G2/M Arrest

Sequence comparison among the members of the GADD45 family indicates that greater than 50% of the residues are conserved. The center region (residues 35–108) shares 55% identical and 81% similar residues. A series of deletion mutants were made with deletions at the N-terminus, the C-terminus and the central region. These mutants were transiently transfected into 293 cells or the HCT116 cell line, and the levels of expression were determined by Western blot or by immunoprecipitation and followed by Western blot analysis. All mutants expressed appreciable amounts of proteins of the appropriate sizes in COS-7 cells as detected by anti-HA antibody. Interestingly, the full length GADD45-HA fusion gene produced two bands, with the upper band corresponding to the molecular weight of full length GADD45, while the lower band was identical to the mutant 16–165. Both bands were also detected by anti-GADD45 antibody. These fusion genes produced identical protein patterns in HCT116 cells. Because codon 16 of GADD45 encodes a methionine, and the start codon of the fusion gene was very close to the CMV promoter, it is likely that the second methionine is serving as a secondary transcription start site. This may also account for the second band seen with the 1–108 mutant.

The ability of these deletion mutants to induce G2/M arrest in primary human fibroblasts was assayed. The G2/M arrest was monitored by cell morphology 24 hr following expression of the GADD45 constructs. The correlation of cell morphology and G2/M arrest was previously confirmed by the expression of a mitotic marker MPM2, 4N DNA contents and the flow cytometry analysis. (Wang, X. W., et al., *Proc. Natl. Acad. Sci U.S.A.* 96:3706–3711 (1999).) Consistent with previously published data (Wang, X. W., et al. *Proc. Natl. Acad. Sci. U.S.A.* 96:3706–3711 (1999); Zhan, Q., et al. *Oncogene* 18:2892–2900 (1999); Zhan, Q., et al., *Mol. Cell Biol.* 14:2361–2371 (1994)), the HA-tagged full length GADD45 (1–165) induced both G2/M arrest and growth suppression. Deletion of either the N-terminal 16 residues (16–165) or the C-terminal 57 residues (1–108) did not change the results, suggesting that these domains are dispensable for G2/M arrest. While mutants 1–85, 16–108, 16–85, 35–165 and 35–108 still partially retained activity on G2/M arrest, mutants del50–95 and del50–76 have no detectable activity. These data indicate that the central conserved region between residues 50 and 76 is the functional domain for G2/M arrest.

The central region (residues 50–76) contains many acidic residues. To examine if the acidic residues play an important role in GADD45-mediated G2/M arrest, three additional mutants, M62–67, M74–79 and M82–87, were made in which the residues within these regions were changed to alanines by site-directed mutagenesis. The M82–87 mutant is similar to wild-type GADD45 with regard to its ability to induce a G2/M arrest in normal human fibroblasts, while M74–79 partially lost activity and M62–67 was completely deficient. These data indicate that the DEDDDR (SEQ ID NO:5) motif within residues 62–67 is critical for GADD45-mediated G2/M arrest.

Example 8

Ability of the GADD45 Mutants to Bind to Cdc2, PCNA or p21$^{waf1}$ Proteins

To determine whether the GADD45 mutants associate with Cdc2, PCNA or p21$^{waf1}$ in vivo, HCT116 cells were transiently transfected with HA-tagged GADD45 mutant expression vectors. Cell lysates were immunoprecipitated with antibodies to Cdc2, PCNA or p21$^{waf1}$. The immunoprecipitates were then analyzed by Western blot with anti-HA antibody. The specificity and efficiency of each antibody to immunoprecipitate Cdc2, PCNA and p21$^{waf1}$ was verified by Western blot of the same membrane with the corresponding antibody. Consistent with previously-published data, transfected wild type GADD45 co-immunoprecipitated with Cdc2, PCNA, and p21$^{waf1}$ antibodies. The binding was abolished completely by removal of the central region (mutant del50–76). These data indicate the domain that interacts with Cdc2, PCNA or p21$^{waf1}$, includes residues 50–76 of GADD45. The three site-mutagenesis mutants (M62–67, M74–79, M82–87) can still bind to Cdc2, PCNA and p21$^{waf1}$, although M62–67 binding is slightly reduced. This suggests that residues 62–67 may be a part of the actual interaction domain with Cdc2, PCNA, and p21$^{waf1}$.

Example 9

Ability of GADD45 Mutants to Inhibit Cdc2 Kinase

To test whether radiation alters the Cdc2 kinase activity, RKO cells were irradiated with 6.5 Gy IR and incubated for 1, 4 or 24 h. Cell lysates were prepared, and the Cdc2/cyclin B1 complex was immunoprecipitated with cyclin B1 antibody. Cdc2 kinase activity was measured using the substrate histone H1. Anti-mouse IgG was used as a control. Levels of the Cdc2/cyclin B1 kinase activity were similar in the unirradiated cells during the incubation period. RKO cells showed a strong reduction in Cdc2 kinase activity 1 h incubation after irradiation, but activity returned to the normal level by 4 h and was further increased at 24 h. Cell cycle analysis using cell sorting done in parallel indicated that IR-induced a G2/M arrest as early as 4 h after treatment, but significantly increased through 24 h. These data indicate that whereas immediate G2/M arrest may involve inactivation of Cdc2 kinase activity, the prolonged arrest may require additional processes.

To test whether GADD45 mutants inhibited Cdc2 kinase activity in vivo, RKO cells were transfected with wild-type and mutant GADD45. The Cdc2 kinase activity was then determined as described above. GADD45 inhibited the Cdc2 kinase activity within 6 h of transfection, consistent with previously published data (Zhan, Q. et al., (1999), Oncogene 18:2892–2900). Interestingly, the inhibition was reversed within 24 h. In contrast, mutants M62–67 and del50–76 have no inhibitory effect on the Cdc2 kinase following 6 h transfection.

Example 10

GADD45β and GADD45γ Do Not Induce a G2/M Arrest

In mammalian cells, at least two additional GADD45 family members, GADD45β and GADD45γ have been identified based on their extensive sequence conservation and their induction following DNA damage and/or other environmental stresses. (Takekawa, M. and H. Saito, *Cell* 95:521–530 (1998).) The central regions of these proteins share more than 80% sequence homology with GADD45. Similar to GADD45, both proteins also bind to Cdc2 in vivo. Surprisingly, as set forth below, we found that only GADD45 is able to induce a G2/M arrest and to inhibit the Cdc2/cyclin B1 kinase, while neither GADD45β nor GADD45γ have such activity. The data reported below indicate that the binding of these proteins to Cdc2 is insufficient to regulate the transition from G2 to mitosis. One possibility for the lack of G2/M arrest by either GADD45β or GADD45γ is that GADD45 is a nuclear protein (Kearsey, J. M., et al., *Oncogene* 11:1675–1683 (1995); Smith, M. L., et al., *Science* 266:1376–1380 (1994)), while GADD45β and GADD45γ have been shown to be localized in cytoplasm and to activate the MAPK (mitogen-activated protein kinase) cascade. (Takekawa, M. and H. Saito, *Cell* 95:521–530 (1998).) Alternatively, only GADD45 contains the DEDDDR motif and this motif may provide a unique mechanism to induce a G2/m arrest. Therefore, members of the GADD45 family may not act redundantly in the regu lation of the G2/M checkpoint and additional functions may be associated with GADD45β and GADD45γ in their ability to bind to Cdc2.

To examine whether other GADD45 family members are involved in the G2 checkpoint, normal primary human fibroblasts were microinjected with GADD45, GADD45β or GADD45γ expression vector. While GADD45 predominantly induced a G2/M arrest, no arrest was observed with the expression of either GADD45β or GADD45γ. To determine if the GADD45 family members associate with Cdc2 in vivo, HCT116 cells were transfected with HA-tagged expression vectors and immunoprecipitated with anti-Cdc2 antibody. Following immunoblot analysis, the HA-tagged GADD45 family proteins were detected with the anti-HA antibody. The results indicate that GADD45β and GADD45γ are able to bind to Cdc2 in vivo, but were unable to inhibit its kinase activity.

Example 11

Interactions with other Proteins Involved in G2/M Checkpoints

One of the key steps in regulating the progression of mammalian cells from G2 into mitosis is the activation of the G2-specific Cdc2/cyclin B1 kinase. (King, R. W., et al., Cell 79:563–571 (1994); Nurse, P. Cell 79:547–550 (1994).) p53 plays an essential role in G2/M checkpoints. Interestingly, the proteins of three p53-regulated genes, $p21^{waf1}$, 14-3-3σ and GADD45, are involved in G2/M checkpoints. (Bunz, F., A., et al., Science 282:1497–1501 (1998); Chan, T. A., et al., Nature 401:616–620 (1999); Wang, X. W., et al. Proc. Natl. Acad. Sci USA. 96:3706–3711 (1999).) Both $p^{21waf1}$ and 14-3-3σ may initiate a G2/M arrest through direct binding to and sequestering Cdc2 in the cytoplasm, thereby preventing Cdc2/cyclin B1 from becoming activated and initiating mitosis. (Chan, T. A., et al., Nature 401:616–620 (1999).) GADD45 physically interacts with Cdc2 and directly inhibits Cdc2/cyclin B1 kinase through its disruption of the Cdc2/cyclin B1 complex. (Zhan, Q., et al., Oncogene 18:2892–2900 (1999).) Our data indicate that GADD45 may be involved in a G2/M checkpoint at least partially through direct inactivation of the Cdc2/cyclin B1 kinase activity.

These findings suggest that the G2/M checkpoint may utilize a redundant system. It has been reported that GADD45 interacts with the nuclear proteins $p21^{waf1}$ and PCNA. (Kearsey, J. M., et al., Oncogene 11: 1675–1683 (1995); Smith, M. L., et al., Science 266:1376–1380 (1994).) GADD45 can disrupt the ability of $p21^{waf1}$ to bind to PCNA, and, conversely, $p21^{waf1}$ blocks the ability of GADD45 to bind to PCNA. (Chen, I. T., et al., Oncogene 11:1931–1937 (1995).) Although the central region (residues 50–76) of GADD45 is required for interaction with both Cdc2 and $p21^{waf1}$, the mutant M62–67 that lost its inhibitory effect on the Cdc2/cyclin B1 kinase can still bind to Cdc2 and $p21^{waf1}$. Moreover, $p21^{waf1}$ is not required for GADD45-induced G2/M arrest. (Wang, X. W., et al., Proc. Natl. Acad. Sci U.S.A. 96:3706–3711 (1999).) Therefore, the binding of GADD45 to Cdc2 and $p21^{waf1}$ is insufficient to define the mechanism of a GADD45-mediated G2/M checkpoint. The additional activity of the DEDDDR (SEQ ID NO:5) motif is needed to inactivate the Cdc2/cyclin B1 kinase and to induce a G2/M arrest. In addition, the GADD45-mediated G2/M checkpoint is independent of 14-3-3σ because overexpression of GADD45 is still able to induce a G2/M arrest in 14-3-3σ-deficient HCT116 cells (gift of Dr. Bert Vogelstein). These data indicate that three p53 downstream genes may utilize different mechanisms to activate the G2/M checkpoints.

It is understood that the examples and embodiments described herein are for illustrative purposes only and that various modifications or changes in light thereof will be suggested to persons skilled in the art and are to be included within the spirit and purview of this application and scope of the appended claims. All publications, GenBank sequences, ATCC deposits, patents, and patent applications cited herein are hereby incorporated by reference in their entirety for all purposes.

What is claimed is:

1. An isolated polypeptide comprising a sequence of DEDDDR (SEQ ID NO: 5) and having no more than about 25 amino acids at either the N-terminal or C-terminal of the sequence of DEDDDR (SEQ ID NO: 50), wherein the polypeptide inhibits GADD45 activity by at least 10%.

2. The polypeptide of claim 1, which comprises a sequence of DEDDDRD (SEQ ID NO: 50).

3. The polypeptide of claim 1, which is a fragment of SEQ ID NO:2.

4. The polypeptide of claim 1, which has no more than about 20 amino acids at the N-terminal or C-terminal of the sequence of DEDDDR (SEQ ID NO: 50).

5. The polypeptide of claim 4, which has no more than about 10 amino acids at the N-terminal or C-terminal of the sequence of DEDDDR (SEQ ID NO: 50).

6. A polypeptide of claim 1, which consists of a sequence selected from the group consisting of:

```
                                                    (SEQ ID NO:16)
EAAKLLNVDPDNVVLCLLAADEDDDRDVALQIHFTLIQAFCCENDI;

(SEQ ID NO:17)
LLNVDPDNVVLCLLAADEDDDRDVALQIHFTLIQAFCC;

(SEQ ID NO:18)
DNVVLCLLAADEDDDRDVALQIHFTL;

(SEQ ID NO:19)
CLLAADEDDDRDVALQIHFTL;

(SEQ ID NO:20)
DNVVLCLLAADEDDDRDVALQ;

(SEQ ID NO:21)
EAAKLLNVDPDNVVLCLLAADEDDDR;

(SEQ ID NO:22)
DEDDDRDVALQIHFTLIQAFCCENDI;

(SEQ ID NO:23)
ADEDDDRDVALQIHFTLIQAFCCENDI;

(SEQ ID NO:24)
ADEDDDRDVALQIHFTL;

(SEQ ID NO:25)
ADEDDDRDVALQ;

(SEQ ID NO:5)
DEDDDR;

(SEQ ID NO:26)
ADEDDDR;

(SEQ ID NO:27)
DNVVLCLLAADEDDDR;

(SEQ ID NO:28)
CLLAADEDDDR;

(SEQ ID NO:29)
CLLAADEDDDRD;

(SEQ ID NO:30)
CLLAADEDDDRDVAL;

(SEQ ID NO:31)
DNVVLCLLAADEDDDRDVALQIHFTLIQAFCCENDI;
and
                                                    (SEQ ID NO:32)
LNVDPDNVVLCLLAADEDDDRDVALQIHFTLIQAFCCENDI.
```

7. A composition comprising the polypeptide of claim 1 in a pharmaceutically acceptable carrier.

8. A composition comprising a liposome comprising the polypeptide of claim 1.

* * * * *

SEQUENCE LISTING

```
<160> NUMBER OF SEQ ID NOS: 32

<210> SEQ ID NO 1
<211> LENGTH: 1343
<212> TYPE: DNA
<213> ORGANISM: Homo sapiens
<220> FEATURE:
<221> NAME/KEY: CDS
<222> LOCATION: (284)..(781)
<223> OTHER INFORMATION: human growth arrest and DNA-damage-inducible
      protein (GADD45)

<400> SEQUENCE: 1
ggcagtggct gggaggcagc ggcccaatta gtgtcgtgcg gcccgtggcg aggcgaggtc      60
cggggagcga gcgagcaagc aaggcgggag gggtggccgg agctgcggcg gctggcacag     120
gaggaggagc ccgggcgggc gaggggcggc cggagagcgc cagggcctga gctgccggag     180
cggcgcctgt gagtgagtgc agaaagcagg cgcccgcgcg ctagccgtgg caggagcagc     240
ccgcacgccg cgctctctcc ctgggcgacc tgcagtttgc aat atg act ttg gag      295
                                               Met Thr Leu Glu
                                                1
```

```
gaa ttc tcg gct gga gag cag aag acc gaa agg atg gat aag gtg ggg    343
Glu Phe Ser Ala Gly Glu Gln Lys Thr Glu Arg Met Asp Lys Val Gly
  5                  10                  15                  20 gat gcc ctg gag gaa gtg ctc agc aaa gcc ctg agt cag cgc acg atc    391
Asp Ala Leu Glu Glu Val Leu Ser Lys Ala Leu Ser Gln Arg Thr Ile
             25                  30                  35 act gtc ggg gtg tac gaa gcg gcc aag ctg ctc aac gtc gac ccc gat    439
Thr Val Gly Val Tyr Glu Ala Ala Lys Leu Leu Asn Val Asp Pro Asp
         40                  45                  50 aac gtg gtg ttg tgc ctg ctg gcg gcg gac gag gac gac gac aga gat    487
Asn Val Val Leu Cys Leu Leu Ala Ala Asp Glu Asp Asp Asp Arg Asp
     55                  60                  65 gtg gct ctg cag atc cac ttc acc ctg atc cag gcg ttt tgc tgc gag    535
Val Ala Leu Gln Ile His Phe Thr Leu Ile Gln Ala Phe Cys Cys Glu
 70                  75                  80 aac gac atc aac atc ctg cgc gtc agc aac ccg ggc cgg ctg gcg gag    583
Asn Asp Ile Asn Ile Leu Arg Val Ser Asn Pro Gly Arg Leu Ala Glu
 85                  90                  95                 100 ctc ctg ctc ttg gag acc gac gct ggc ccc gcg gcg agc gag ggc gcc    631
Leu Leu Leu Leu Glu Thr Asp Ala Gly Pro Ala Ala Ser Glu Gly Ala
                105                 110                 115 gag cag ccc ccg gac ctg cac tgc gtg ctg gtg acg aat cca cat tca    679
Glu Gln Pro Pro Asp Leu His Cys Val Leu Val Thr Asn Pro His Ser
            120                 125                 130 tct caa tgg aag gat cct gcc tta agt caa ctt att tgt ttt tgc cgg    727
Ser Gln Trp Lys Asp Pro Ala Leu Ser Gln Leu Ile Cys Phe Cys Arg
        135                 140                 145 gaa agt cgc tac atg gat caa tgg gtt cca gtg att aat ctc cct gaa    775
Glu Ser Arg Tyr Met Asp Gln Trp Val Pro Val Ile Asn Leu Pro Glu
    150                 155                 160 cgg tga tggcatctga atgaaaataa ctgaaccaaa ttgcactgaa gtttttgaaa      831
Arg
165 tacctttgta gttactcaag cagttactcc ctacactgat gcaaggatta cagaaactga   891 tgccaagggg ctgagtgagt tcaactacat gttctggggg cccggagata gatgactttg   951 cagatggaaa gaggtgaaaa tgaagaagga agctgtgttg aaacagaaaa ataagtcaaa  1011 aggaacaaaa attacaaaga accatgcagg aaggaaaact atgtattaat ttagaatggt  1071 tgagttacat taaaataaac caaatatgtt aaagtttaag tgtgcagcca tagtttgggt  1131 attttttggtt tatatgccct caagtaaaag aaaagccgaa agggttaatc atatttgaaa  1191 accatatttt attgtatttt gatgagatat taaattctca aagttttatt ataaattcta  1251 ctaagttatt ttatgacatg aaaagttatt tatgctataa attttttgaa acacaatacc  1311 tacaataaac tggtatgaat aattgcatca tt                                1343

<210> SEQ ID NO 2
<211> LENGTH: 165
<212> TYPE: PRT
<213> ORGANISM: Homo sapiens

<400> SEQUENCE: 2

Met Thr Leu Glu Glu Phe Ser Ala Gly Glu Gln Lys Thr Glu Arg Met
  1               5                  10                  15

Asp Lys Val Gly Asp Ala Leu Glu Glu Val Leu Ser Lys Ala Leu Ser
             20                  25                  30

Gln Arg Thr Ile Thr Val Gly Val Tyr Glu Ala Ala Lys Leu Leu Asn
         35                  40                  45
```

```
Val Asp Pro Asp Asn Val Val Leu Cys Leu Leu Ala Ala Asp Glu Asp
         50                  55                  60

Asp Asp Arg Asp Val Ala Leu Gln Ile His Phe Thr Leu Ile Gln Ala
 65                  70                  75                  80

Phe Cys Cys Glu Asn Asp Ile Asn Ile Leu Arg Val Ser Asn Pro Gly
                 85                  90                  95

Arg Leu Ala Glu Leu Leu Leu Glu Thr Asp Ala Gly Pro Ala Ala
            100                 105                 110

Ser Glu Gly Ala Glu Gln Pro Pro Asp Leu His Cys Val Leu Val Thr
            115                 120                 125

Asn Pro His Ser Ser Gln Trp Lys Asp Pro Ala Leu Ser Gln Leu Ile
        130                 135                 140

Cys Phe Cys Arg Glu Ser Arg Tyr Met Asp Gln Trp Val Pro Val Ile
145                 150                 155                 160

Asn Leu Pro Glu Arg
                165

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 3
ggcggctcga gactttggag gaattctcgg c                               31

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 4
catcaccgtt cagggagatt aatc                                       24

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:GADD45
      subsequence acidic motif amino acid residues
      62-67; exemplary peptide inhibiting GADD45-related
      dissociation of Cdc2/cyclin B1 complexes

<400> SEQUENCE: 5

Asp Glu Asp Asp Asp Arg
 1               5

<210> SEQ ID NO 6
<211> LENGTH: 160
<212> TYPE: PRT
<213> ORGANISM: Homo sapiens
<220> FEATURE:
<223> OTHER INFORMATION: human growth arrest and DNA-damage-inducible
      protein (hGADD45beta)

<400> SEQUENCE: 6

Met Thr Leu Glu Glu Leu Val Ala Cys Asp Asn Ala Ala Gln Lys Met
```

```
            1               5                   10                  15

Gln Thr Val Thr Ala Ala Val Glu Glu Leu Leu Val Ala Ala Gln Arg
                        20                  25                  30

Gln Asp Arg Leu Thr Val Gly Val Tyr Glu Ser Ala Lys Leu Met Asn
                        35                  40                  45

Val Asp Pro Asp Ser Val Val Leu Cys Leu Leu Ala Ile Asp Glu Glu
                        50                  55                  60

Glu Glu Asp Asp Ile Ala Leu Gln Ile His Phe Thr Leu Ile Gln Ser
        65                  70                  75                  80

Phe Cys Cys Asp Asn Asp Ile Asn Ile Val Arg Val Ser Gly Met Gln
                        85                  90                  95

Arg Leu Ala Gln Leu Leu Gly Glu Pro Ala Glu Thr Gln Gly Thr Thr
                        100                 105                 110

Glu Ala Arg Asp Leu His Cys Leu Leu Val Thr Asn Pro His Thr Asp
                        115                 120                 125

Ala Trp Lys Ser His Gly Leu Val Glu Val Ala Ser Tyr Cys Glu Glu
                        130                 135                 140

Ser Arg Gly Asn Asn Gln Trp Val Pro Tyr Ile Ser Leu Gln Glu Arg
        145                 150                 155                 160

<210> SEQ ID NO 7
    <211> LENGTH: 159
    <212> TYPE: PRT
    <213> ORGANISM: Homo sapiens
    <220> FEATURE:
    <223> OTHER INFORMATION: human growth arrest and DNA-damage-inducible
          protein (hGADD45gamma)

<400> SEQUENCE: 7

Met Thr Leu Glu Glu Val Arg Gly Gln Asp Thr Val Pro Glu Ser Thr
    1               5                   10                  15

Ala Arg Met Gln Gly Ala Gly Lys Ala Leu His Glu Leu Leu Leu Ser
                    20                  25                  30

Ala Gln Arg Gln Gly Cys Leu Thr Ala Gly Val Tyr Glu Ser Ala Lys
                    35                  40                  45

Val Leu Asn Val Asp Pro Asp Asn Val Thr Phe Cys Val Leu Ala Ala
                    50                  55                  60

Gly Glu Glu Asp Glu Gly Asp Ile Ala Leu Gln Ile His Phe Thr Leu
    65                  70                  75                  80

Ile Gln Ala Phe Cys Cys Glu Asn Asp Ile Asp Ile Val Arg Val Gly
                    85                  90                  95

Asp Val Gln Arg Leu Ala Ala Ile Val Gly Ala Gly Glu Glu Ala Gly
                    100                 105                 110

Ala Pro Gly Asp Leu His Cys Ile Leu Ile Ser Asn Pro Asn Glu Asp
                    115                 120                 125

Ala Trp Lys Asp Pro Ala Leu Glu Lys Leu Ser Leu Phe Cys Glu Glu
                    130                 135                 140

Ser Arg Ser Val Asn Asp Trp Val Pro Ser Ile Thr Leu Pro Glu
    145                 150                 155

<210> SEQ ID NO 8
    <211> LENGTH: 165
    <212> TYPE: PRT
    <213> ORGANISM: Mus musculus
    <220> FEATURE:
    <223> OTHER INFORMATION: mouse growth arrest and DNA-damage-inducible
          protein (mGADD45)
```

```
<400> SEQUENCE: 8

Met Thr Leu Glu Glu Phe Ser Ala Ala Glu Gln Lys Thr Glu Arg Met
 1               5                  10                  15

Asp Thr Val Gly Asp Ala Leu Glu Glu Val Leu Ser Lys Ala Arg Ser
            20                  25                  30

Gln Arg Thr Ile Thr Val Gly Val Tyr Glu Ala Ala Lys Leu Leu Asn
        35                  40                  45

Val Asp Pro Asp Asn Val Val Leu Cys Leu Leu Ala Ala Asp Glu Asp
    50                  55                  60

Asp Asp Arg Asp Val Ala Leu Gln Ile His Phe Thr Leu Ile Arg Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Glu Asn Asp Ala Gly Pro Ala Glu
            100                 105                 110

Ser Gly Gly Ala Ala Gln Thr Pro Asp Leu His Cys Val Leu Val Thr
        115                 120                 125

Asn Pro His Ser Ser Gln Trp Lys Asp Pro Ala Leu Ser Gln Leu Ile
    130                 135                 140

Cys Phe Cys Arg Glu Ser Arg Tyr Met Asp Gln Trp Val Pro Val Ile
145                 150                 155                 160

Asn Leu Pro Glu Arg
            165

<210> SEQ ID NO 9
<211> LENGTH: 165
<212> TYPE: PRT
<213> ORGANISM: Rattus norvegicus
<220> FEATURE:
<223> OTHER INFORMATION: rat growth arrest and DNA-damage-inducible
      protein (rGADD45)

<400> SEQUENCE: 9

Met Thr Leu Glu Glu Phe Ser Ala Ala Glu Gln Lys Ile Glu Arg Met
 1               5                  10                  15

Asp Thr Val Gly Asp Ala Leu Glu Glu Val Leu Ser Lys Ala Arg Ser
            20                  25                  30

Gln Arg Thr Ile Thr Val Gly Val Tyr Glu Ala Ala Lys Leu Leu Asn
        35                  40                  45

Val Asp Pro Asp Asn Val Val Leu Cys Leu Leu Ala Ala Asp Glu Asp
    50                  55                  60

Asp Asp Arg Asp Val Ala Leu Gln Ile His Phe Thr Leu Ile Arg Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Leu Glu Asn Asp Lys Ser Pro Ala Glu
            100                 105                 110

Ser Gly Gly Leu Ala Gln Thr Pro Asp Leu His Cys Val Leu Val Thr
        115                 120                 125

Asn Pro His Ser Ser Gln Trp Lys Asp Pro Ala Leu Ser Gln Leu Ile
    130                 135                 140

Cys Phe Cys Arg Glu Ser Arg Tyr Met Asp Gln Trp Val Pro Val Ile
145                 150                 155                 160

Asn Leu Pro Glu Arg
            165
```

```
<210> SEQ ID NO 10
<211> LENGTH: 34
<212> TYPE: PRT
<213> ORGANISM: Homo sapiens
<220> FEATURE:
<223> OTHER INFORMATION: human GADD45 residues 58-91

<400> SEQUENCE: 10

Leu Leu Ala Ala Asp Glu Asp Asp Asp Arg Asp Val Ala Leu Gln Ile
 1               5                  10                  15

His Phe Thr Leu Ile Gln Ala Phe Cys Cys Glu Asn Asp Ile Asn Ile
            20                  25                  30

Leu Arg

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence:human GADD45
      residues 58-91 with residues 62-67 changed to Ala
      by site-directed mutagenesis (M62-67)

<400> SEQUENCE: 11

Leu Leu Ala Ala Ala Ala Ala Ala Ala Ala Asp Val Ala Leu Gln Ile
 1               5                  10                  15

His Phe Thr Leu Ile Gln Ala Phe Cys Cys Glu Asn Asp Ile Asn Ile
            20                  25                  30

Leu Arg

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence:human GADD45
      residues 58-91 with residues 74-79 changed to Ala
      by site-directed mutagenesis (M74-79)

<400> SEQUENCE: 12

Leu Leu Ala Ala Asp Glu Asp Asp Asp Arg Asp Val Ala Leu Gln Ile
 1               5                  10                  15

Ala Ala Ala Ala Ala Ala Ala Phe Cys Cys Glu Asn Asp Ile Asn Ile
            20                  25                  30

Leu Arg

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence:human GADD45
      residues 58-91 with residues 82-87 changed to Ala
      by site-directed mutagenesis (M82-87)

<400> SEQUENCE: 13

Leu Leu Ala Ala Asp Glu Asp Asp Asp Arg Asp Val Ala Leu Gln Ile
 1               5                  10                  15

His Phe Thr Leu Ile Gln Ala Phe Ala Ala Ala Ala Ala Ala Asn Ile
            20                  25                  30

Leu Arg
```

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Ran small
      nuclear GTPase carboxy-terminal domain closely
      related acidic motif

<400> SEQUENCE: 14

Asp Glu Asp Asp Asp Leu
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:GADD45
      acidic motif residues 62-69

<400> SEQUENCE: 15

Asp Glu Asp Asp Asp Arg Asp
 1               5

<210> SEQ ID NO 16
<211> LENGTH: 46
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 16

Glu Ala Ala Lys Leu Leu Asn Val Asp Pro Asp Asn Val Val Leu Cys
 1               5                  10                  15

Leu Leu Ala Ala Asp Glu Asp Asp Asp Arg Asp Val Ala Leu Gln Ile
             20                  25                  30

His Phe Thr Leu Ile Gln Ala Phe Cys Cys Glu Asn Asp Ile
         35                  40                  45

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 17

Leu Leu Asn Val Asp Pro Asp Asn Val Val Leu Cys Leu Leu Ala Ala
 1               5                  10                  15

Asp Glu Asp Asp Asp Arg Asp Val Ala Leu Gln Ile His Phe Thr Leu
             20                  25                  30

Ile Gln Ala Phe Cys Cys
         35

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

```
<400> SEQUENCE: 18

Asp Asn Val Val Leu Cys Leu Leu Ala Ala Asp Glu Asp Asp Asp Arg
  1               5                  10                  15

Asp Val Ala Leu Gln Ile His Phe Thr Leu
             20                  25

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 19

Cys Leu Leu Ala Ala Asp Glu Asp Asp Asp Arg Asp Val Ala Leu Gln
  1               5                  10                  15

Ile His Phe Thr Leu
             20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 20

Asp Asn Val Val Leu Cys Leu Leu Ala Ala Asp Glu Asp Asp Asp Arg
  1               5                  10                  15

Asp Val Ala Leu Gln
             20

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 21

Glu Ala Ala Lys Leu Leu Asn Val Asp Pro Asp Asn Val Val Leu Cys
  1               5                  10                  15

Leu Leu Ala Ala Asp Glu Asp Asp Asp Arg
             20                  25

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 22

Asp Glu Asp Asp Asp Arg Asp Val Ala Leu Gln Ile His Phe Thr Leu
  1               5                  10                  15

Ile Gln Ala Phe Cys Cys Glu Asn Asp Ile
```

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 23

Ala Asp Glu Asp Asp Asp Arg Asp Val Ala Leu Gln Ile His Phe Thr
 1               5                  10                  15

Leu Ile Gln Ala Phe Cys Cys Glu Asn Asp Ile
            20                  25

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 24

Ala Asp Glu Asp Asp Asp Arg Asp Val Ala Leu Gln Ile His Phe Thr
 1               5                  10                  15

Leu

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 25

Ala Asp Glu Asp Asp Asp Arg Asp Val Ala Leu Gln
 1               5                  10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 26

Ala Asp Glu Asp Asp Asp Arg
 1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 27

Asp Asn Val Val Leu Cys Leu Leu Ala Ala Asp Glu Asp Asp Asp Arg
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 28

Cys Leu Leu Ala Ala Asp Glu Asp Asp Asp Arg
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 29

Cys Leu Leu Ala Ala Asp Glu Asp Asp Asp Arg Asp
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 30

Cys Leu Leu Ala Ala Asp Glu Asp Asp Asp Arg Asp Val Ala Leu
1               5                   10                  15

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes

<400> SEQUENCE: 31

Asp Asn Val Val Leu Cys Leu Leu Ala Ala Asp Glu Asp Asp Asp Arg
1               5                   10                  15

Asp Val Ala Leu Gln Ile His Phe Thr Leu Ile Gln Ala Phe Cys Cys
            20                  25                  30

Glu Asn Asp Ile
            35

<210> SEQ ID NO 32
<211> LENGTH: 41
<212> TYPE: PRT
<213> ORGANISM: Artificial Sequence
<220> FEATURE:
<223> OTHER INFORMATION: Description of Artificial Sequence:exemplary
      peptide inhibiting GADD45-related dissociation of
      Cdc2/cyclin B1 complexes -continued

```
<400> SEQUENCE: 32

Leu Asn Val Asp Pro Asp Asn Val Val Leu Cys Leu Leu Ala Ala Asp
 1               5                  10                  15

Glu Asp Asp Arg Asp Val Ala Leu Gln Ile His Phe Thr Leu Ile
             20                  25                  30

Gln Ala Phe Cys Cys Glu Asn Asp Ile
             35                  40
```